United States Patent
Leadbetter

(10) Patent No.: US 7,208,471 B2
(45) Date of Patent: *Apr. 24, 2007

(54) GLYCOPEPTIDE PHOSPHONATE DERIVATIVES

(75) Inventor: Michael R. Leadbetter, San Leandro, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/265,570

(22) Filed: Nov. 2, 2005

(65) Prior Publication Data

US 2006/0063706 A1  Mar. 23, 2006

Related U.S. Application Data

(63) Continuation of application No. 11/037,934, filed on Jan. 18, 2005, now Pat. No. 7,008,923, which is a continuation of application No. 10/669,778, filed on Sep. 24, 2003, now Pat. No. 6,887,976, which is a continuation of application No. 09/847,042, filed on May 1, 2001, now Pat. No. 6,635,618.

(60) Provisional application No. 60/213,410, filed on Jun. 22, 2000.

(51) Int. Cl.
*A61K 38/14* (2006.01)
*C07K 9/00* (2006.01)

(52) U.S. Cl. ............................ 514/7; 514/8; 530/317; 530/322

(58) Field of Classification Search .................... None
See application file for complete search history.

(56) References Cited

U.S. PATENT DOCUMENTS

| | | | |
|---|---|---|---|
| 4,643,987 A | 2/1987 | Nagarajan et al. | |
| 4,698,327 A | 10/1987 | Nagarajan et al. | |
| 4,727,064 A | 2/1988 | Pitha | |
| 4,983,586 A | 1/1991 | Bodor | |
| 5,024,998 A | 6/1991 | Bodor | |
| 5,217,493 A | 6/1993 | Raad et al. | |
| 5,591,714 A | 1/1997 | Nagarajan et al. | |
| 5,602,112 A | 2/1997 | Rubinfeld | |
| 5,750,509 A | 5/1998 | Malabarba et al. | |
| 5,840,684 A | 11/1998 | Cooper et al. | |
| 5,916,873 A | 6/1999 | Cooper et al. | |
| 6,111,084 A | 8/2000 | Wong et al. | |
| 6,323,176 B1 | 11/2001 | Jamison et al. | |
| 6,392,012 B1 | 5/2002 | Judice et al. | |
| 6,635,618 B2 | 10/2003 | Leadbetter et al. | |
| 6,872,701 B2 | 3/2005 | Leadbetter et al. | |
| 6,887,976 B2 | 5/2005 | Leadbetter et al. | |
| 6,979,723 B2 * | 12/2005 | Leadbetter et al. | ......... 530/322 |
| 7,008,923 B2 * | 3/2006 | Leadbetter et al. | ............. 514/7 |
| 7,015,307 B2 * | 3/2006 | Schmidt et al. | ............. 530/330 |
| 7,074,890 B2 * | 7/2006 | Leadbetter et al. | ......... 530/322 |
| 2005/0164916 A1 | 7/2005 | Leadbetter et al. | |

FOREIGN PATENT DOCUMENTS

| | | |
|---|---|---|
| EP | 0 667 353 A1 | 8/1995 |
| EP | 0 816 378 A1 | 1/1998 |
| JP | 2000-302687 | 10/2000 |
| WO | WO 94/12217 | 6/1994 |
| WO | WO 00/04044 | 1/2000 |
| WO | WO 00/39156 | 7/2000 |
| WO | WO 00/54751 | 9/2000 |
| WO | WO 00/59528 | 10/2000 |
| WO | WO 01/82971 A1 | 11/2001 |
| WO | WO 01/83520 A2 | 11/2001 |
| WO | WO 01/97851 A2 | 12/2001 |
| WO | WO 01/98326 A2 | 12/2001 |
| WO | WO 01/98327 A2 | 12/2001 |
| WO | WO 01/98329 A1 | 12/2001 |

OTHER PUBLICATIONS

Allen et al., "The Role of Hydrophobic Side Chains as Determinants of Antibacterial Activity of Semisynthetic Glycopeptide Antibiotics", The Journal of Antibiotics, vol. 50, No. 8, pp. 677-684 (1997).
GE et al., "Vancomycin Derivatives That Inhibit Peptidoglycan Biosynthesis Without Binding D-Ala-D-Ala", Science, vol. 284, pp. 507-511 (1999).
Malabarba et al., "New Semisynthetic Glycopeptides MDL 63,246 and MDL 63,042, and Other Amide Derivatives of Antibiotic A-40, 926 Active against Highly Glycopeptide-resistant VanA Enterococci", The Journal of Antibiotics, vol. 48, No. 8, pp. 869-883 (1995).
Nagarajan et al., "Synthesis and Antibacterial Evaluation of N-Alkyl Vancomycins", The Journal of Antibiotics, vol. XLII, No. 1, pp. 63-72 (1989).

(Continued)

*Primary Examiner*—Jeffrey Edwin Russel
(74) *Attorney, Agent, or Firm*—Jeffrey A. Hagenah

(57) ABSTRACT

Disclosed are glycopeptides that are substituted with one or more substituents each comprising one or more phosphono groups; and pharmaceutical compositions containing such glycopeptide derivatives. The disclosed glycopeptide derivatives are useful as antibacterial agents.

5 Claims, No Drawings

OTHER PUBLICATIONS

Nicolaou et al., "Chemistry, Biology and Medicine of the Glycopeptide Antibiotics", Angew. Chem. Int. Ed., vol. 38, pp. 2097-2152 (1999).

Pavlov et al., "A New Type of Chemical Modification of Glycopeptides Antibiotics: Aminomethylated Derivatives of Eremomycin and Their Antibacterial Activity", The Journal of Antibiotics, vol. 50, No. 6, pp. 509-513 (1997).

Pavlov et al., "Chemical Modification of Glycopeptide Antibiotics [VC1]", Russian Journal of Bioorganic Chemistry, vol. 24, No. 9, pp. 570-587 (1998).

Pavlov et al., "Mono and Double Modified Teicoplanin Aglycon Derivatives on the Amino Acid No. 7; Structure-activity Relationship", The Journal of Antibiotics, vol. 51, No. 1, pp. 73-78 (1998).

Zhang et al., "A review of recent applications of cyclodextrins for drug discovery", Expert Opinion on Therapeutic Patents, vol. 9, No. 12, 21 pages (1999).

deBree et al., "Structure-Function Relationships of the Vasopressin Prohormone Domains", Cellular and Molecular Neurobiology, vol. 18, No. 2, pp. 173-191 (1998).

Sears et al., "Intervention of carbohydrate recognition by proteins and nucleic acids", Proc. Natl. Acad. Sci. USA, vol. 93, pp. 12086-12093 (Oct. 1996).

Lampe et al., "Parallel Synthesi of Sialyl Lewis X Mimetics on a Solid Phase: Access to a Library of Fucopeptides", Angew. Chem. Int. Ed., vol. 37, No. 12, pp. 1707-1711 (1998).

\* cited by examiner

GLYCOPEPTIDE PHOSPHONATE DERIVATIVES

CROSS-REFERENCE TO RELATED APPLICATIONS

This application is a continuation of U.S. application Ser. No. 11/037,934, filed 18 Jan. 2005 now U.S. Pat. No. 7,008,923; which application is a continuation of U.S. application Ser. No. 10/669,778, filed 24 Sep. 2003 (now U.S. Pat. No. 6,887,976 B2); which application is a continuation of U.S. application Ser. No. 09/847,042, filed 01 May 2001 (now U.S. Pat. No. 6,635,618 B2); which application claims the benefit of U.S. Provisional Application No. 60/213,410, filed 22 Jun. 2000; which applications are incorporated herein by reference in their entirety.

BACKGROUND OF THE INVENTION

1. Field of the Invention

This invention is directed to novel phosphonate derivatives of glycopeptide antibiotics and related compounds. This invention is also directed to pharmaceutical compositions containing such glycopeptide phosphonate derivatives, methods of using such glycopeptide phosphonate derivatives as antibacterial agents, and processes and intermediates useful for preparing such glycopeptide phosphonate derivatives.

2. Background

Glycopeptides (e.g. dalbaheptides) are a well-known class of antibiotics produced by various microorganisms (see *Glycopeptide Antibiotics,* edited by R. Nagarajan, Marcel Dekker, Inc. New York (1994)). These complex multi-ring peptide compounds are very effective antibacterial agents against a majority of Gram-positive bacteria. Although potent antibacterial agents, the glycopeptides antibiotics are not used in the treatment of bacterial diseases as often as other classes of antibiotics, such as the semi-synthetic penicillins, cephalosporins and lincomycins, due to concerns regarding toxicity.

In recent years, however, bacterial resistance to many of the commonly-used antibiotics has developed (see J. E. Geraci et al., *Mayo Clin. Proc.* 1983, 58, 88–91; and M. Foldes, *J. Antimicrob. Chemother.* 1983, 11, 21–26). Since glycopeptide antibiotics are often effective against these resistant strains of bacteria, glycopeptides such as vancomycin have become the drugs of last resort for treating infections caused by these organisms. Recently, however, resistance to vancomycin has appeared in various microorganisms, such as vancomycin-resistant enterococci (VRE), leading to increasing concerns about the ability to effectively treat bacterial infections in the future (see Hospital Infection Control Practices Advisory Committee, *Infection Control Hospital Epidemiology,* 1995, 17, 364–369; A. P. Johnson et al., *Clinical Microbiology Rev.,* 1990, 3, 280–291; G. M. Eliopoulos, *European J. Clinical Microbiol., Infection Disease,* 1993, 12, 409–412; and P. Courvalin, *Antimicrob. Agents Chemother,* 1990, 34, 2291–2296).

A number of derivatives of vancomycin and other glycopeptides are known in the art. For example, see U.S. Pat. Nos. 4,639,433; 4,643,987; 4,497,802; 4,698,327; 5,591,714; 5,840,684; and 5,843,889. Other derivatives are disclosed in EP 0 802 199; EP 0 801 075; EP 0 667 353; WO 97/28812; WO 97/38702; WO 98/52589; WO 98/52592; and in *J. Amer. Chem. Soc.,* 1996, 118, 13107–13108; *J. Amer. Chem. Soc.,* 1997, 119, 12041–12047; and *J. Amer. Chem. Soc.,* 1994, 116, 4573–4590.

Despite the above referenced disclosures, a need currently exists for novel glycopeptide derivatives having effective antibacterial activity and an improved mammalian safety profile. In particular, a need exists for glycopeptide derivatives which are effective against a wide spectrum of pathogenic microorganism, including vancomycin-resistant microorganisms, and which have reduced tissue accumulation and/or nephrotoxicity.

SUMMARY OF THE INVENTION

The present invention provides novel glycopeptide phosphonate derivatives having highly effective antibacterial activity and an improved mammalian safety profile. More specifically, the glycopeptide phosphonate derivatives of the invention unexpectedly exhibit reduced tissue accumulation and/or nephrotoxicity when administered to a mammal.

Accordingly, this invention provides glycopeptide compounds substituted with one or more (e.g., 1, 2 or 3) substituents comprising one or more (e.g., 1, 2 or 3) phosphono ($-PO_3H_2$) groups; or a pharmaceutically acceptable salt, stereoisomer, or prodrug thereof Preferably, the glycopeptide compound is substituted with one or two substituents comprising one or two phosphono groups. More preferably, the glycopeptide compound is substituted with one substituent comprising one or two phosphono groups, preferably one phosphono group. Optionally, the glycopeptide compounds of this invention may also be substituted with other substituents not comprising a phosphono group, provided that at least one substituent comprises one or more phosphono groups.

Accordingly, in one preferred embodiment, this invention provides a glycopeptide compound substituted at the C-terminus with a substituent comprising one or two phosphono ($-PO_3H_2$) groups; or a pharmaceutically acceptable salt, stereoisomer, or prodrug thereof. Preferably, the phosphono-containing substituent is attached to the carbonyl group at the C-terminus through an amide bond, an ester bond, or a thioester bond; more preferably, through an amide bond. Preferably, the phosphono-containing substituent comprises one phosphono group. Particularly preferred phosphono-containing substituents at the C-terminus include phosphonomethylamino, 3-phosphonopropylamino and 2-hydroxy-2-phosphonoethylamino.

In another preferred embodiment, this invention provides a glycopeptide compound substituted at the R-terminus (on the resorcinol ring) with a substituent comprising one or two phosphono ($-PO_3H_2$) groups; or a pharmaceutically acceptable salt, stereoisomer, or prodrug thereof. Preferably, the phosphono-containing substituent is attached to the R-terminus (i.e., the resorcinol ring) through the nitrogen atom of an aminomethyl group attached to the R-terminus. Preferably, the phosphono-containing substituent comprises one phosphono group. Particularly preferred phosphono-containing substituents at the R-terminus include N-(phosphonomethyl)aminomethyl; -(2-hydroxy-2-phosphonoethyl)aminomethyl; N-carboxymethyl-N-(phosphonomethyl)aminomethyl; N,N-bis(phosphonomethyl)aminomethyl; and N-(3-phosphonopropyl) aminomethyl.

In still another preferred embodiment, this invention provides a glycopeptide compound substituted at the C-terminus and at the R-terminus with a substituent comprising one or two phosphono ($-PO_3H_2$) groups; or a pharmaceutically acceptable salt, stereoisomer, or prodrug thereof. Preferably, the phosphono-containing substituents each comprises one phosphono group.

A preferred compound of the invention is a glycopeptide of formula I:

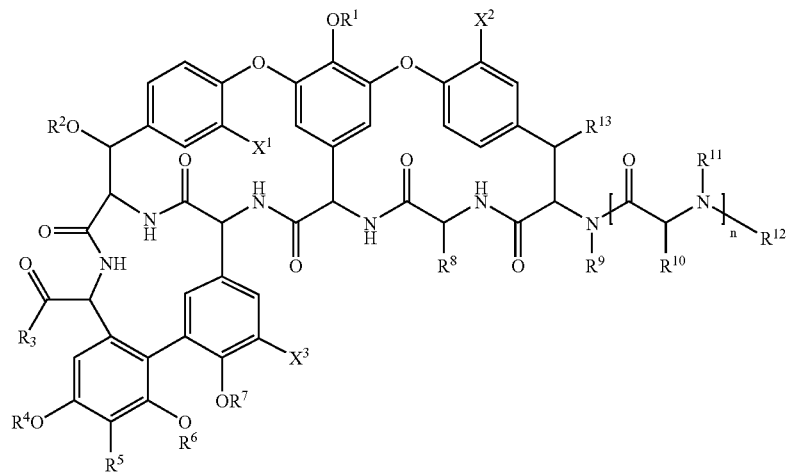

wherein:

R¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —R$^a$—Y—R$^b$-(Z)$_x$; or R¹ is a saccharide group optionally substituted with —R$^a$—Y—R$^b$-(Z)$_x$, R$^f$, —C(O)R$^f$, or —C(O)—R—Y—R$^b$-(Z)$_x$;

R² is hydrogen or a saccharide group optionally substituted with —R$^a$—Y—R$^b$-(Z)$_x$, R$^f$, —C(O)R$^f$, or —C(O)—R$^a$—Y—R$^b$-(Z)$_x$;

R³ is —OR$^c$, —NR$^c$R$^c$, —O—R$^a$—Y—R$^b$-(Z)$_x$, —NR$^c$—R$^a$—Y—R$^b$-(Z)$_x$, —NR$^c$R$^c$, or —O—R$^c$; or R³ is a nitrogen-linked, oxygen-linked, or sulfur-linked substituent that comprises one or more phosphono groups;

R⁴ is selected from the group consisting of hydrogen, alkyl, substituted alkyl, alkenyl, substituted alkenyl, alkynyl, substituted alkynyl, —R$^a$—Y—R$^b$-(Z)$_x$, —C(O)R$^d$ and a saccharide group optionally substituted with —R$^a$—Y—R$^b$-(Z)$_x$, R$^f$, —C(O)R$^f$, or —C(O)—R$^a$—Y—R$^b$-(Z)$_x$, or R⁴ and R⁵ can be joined, together with the atoms to which they are attached, form a heterocyclic ring optionally substituted with —NR$^c$—R$^a$—Y—R$^b$-(Z)$_x$;

R⁵ is selected from the group consisting of hydrogen, halo, —CH(R$^c$)—NR$^c$R$^c$, —CH(R$^c$)—NR$^c$R$^c$, —CH(R$^c$)—NR$^c$—R$^a$—Y—R$^b$-(Z)$_x$, —CH(R$^c$)—R$^x$, —CH(R$^c$)—NR$^c$—R$^a$—C(=O)—R$^x$, and a substituent that comprises one or more phosphono groups;

R⁶ is selected from the group consisting of hydrogen, alkyl, substituted alkyl, alkenyl, substituted alkenyl, alkynyl, substituted alkynyl, —R$^a$—Y—R$^b$-(Z)$_x$, —C(O)R$^d$ and a saccharide group optionally substituted with —R$^a$—Y—R$^b$-(Z)$_x$, R$^f$, —C(O)R$^f$, or —C(O)—R$^a$—Y—R$^b$-(Z)$_x$, or R⁵ and R⁶ can be joined, together with the atoms to which they are attached, form a heterocyclic ring optionally substituted with —NR$^c$—R$^a$—Y—R$^b$-(Z)$_x$;

R⁷ is selected from the group consisting of hydrogen, alkyl, substituted alkyl, alkenyl, substituted alkenyl, alkynyl, substituted alkynyl, —R$^a$—Y—R$^b$-(Z)$_x$, and —C(O)R$^d$;

R⁸ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R⁹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R¹⁰ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or R⁸ and R¹⁰ are joined to form —Ar¹—O—Ar²—, where Ar¹ and Ar² are independently arylene or heteroarylene;

R¹¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or R¹⁰ and R¹¹ are joined, together with the carbon and nitrogen atoms to which they are attached, to form a heterocyclic ring;

R¹² is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, —C(NH)NR$^c$R$^c$, —R$^a$—Y—R$^b$-(Z)$_x$, and —C(O)—R$^a$—Y—R$^b$-(Z)$_x$, or R¹¹ and R¹² are joined, together with the nitrogen atom to which they are attached, to form a heterocyclic ring;

R¹³ is selected from the group consisting of hydrogen or —OR¹⁴;

R¹⁴ is selected from hydrogen, —C(O)R$^d$ and a saccharide group;

each R$^a$ is independently selected from the group consisting of alkylene, substituted alkylene, alkenylene, substituted alkenylene, alkynylene and substituted alkynylene;

each R$^b$ is independently selected from the group consisting of a covalent bond, alkylene, substituted alkylene, alkenylene, substituted alkenylene, alkynylene and substituted alkynylene, provided $R^b$ is not a covalent bond when Z is hydrogen;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^e$ is a saccharide group;

each $R^f$ is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic;

$R^x$ is an N-linked amino saccharide or an N-linked heterocycle;

$X^1$, $X^2$ and $X^3$ are independently selected from hydrogen or chloro;

each Y is independently selected from the group consisting of oxygen, sulfur, —S—S—, —NR$^c$—, —S(O)—, —SO$_2$—, —NR$^c$C(O)—, —OSO$_2$—, —OC(O)—, —NR$^c$SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(=O)—, and —NR$^c$SO$_2$NR$^c$—;

each Z is independently selected from hydrogen, aryl, cycloalkyl, cycloalkenyl, heteroaryl and heterocyclic;

n is 0, 1 or 2; and x is 1 or 2;

or a pharmaceutically acceptable salt, stereoisomer, or prodrug thereof;

provided at least one of $R^3$ and $R^5$ is a substituent comprising one or more phosphono groups.

A preferred compound of the invention is a compound of formula I wherein: $R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —R$^a$—Y—R$^b$-(Z)$_x$; or $R^1$ is a saccharide group optionally substituted with —R$^a$—Y—R$^b$-(Z)$_x$, R$^f$, —C(O)R$^f$, or —C(O)—R$^a$—Y—R$^b$-(Z)$_x$; $R^2$ is hydrogen or a saccharide group optionally substituted with —R$^a$—Y—R$^b$-(Z)$_x$, R$^f$, —C(O)R$^f$, or —C(O)—R$^a$—Y—R$^b$-(Z)$_x$; $R^3$ is —OR$^c$, —NR$^c$R$^c$, —O—R$^a$—Y—R$^b$-(Z)$_x$, NR$^c$—R$^a$—Y-R$^b$-(Z)$_x$, —NR$^c$R$^e$, or —O—R$^e$; or $R^3$ is a nitrogen-linked, oxygen-linked, or sulfur-linked substituent that comprises one or more phosphono groups; $R^4$ is selected from the group consisting of hydrogen, alkyl, substituted alkyl, alkenyl, substituted alkenyl, alkynyl, substituted alkynyl, —R$^a$—Y—R$^b$-(Z)$_x$, —C(O)R$^d$ and a saccharide group optionally substituted with —R$^a$—Y—R$^b$-(Z)$_x$, R$^f$, —C(O)R$^f$, or —C(O)—R$^a$—Y—R$^b$-(Z)$_x$; $R^5$ is selected from the group consisting of hydrogen, halo, —CH(R$^c$)—NR$^c$R$^e$, —CH(R$^c$)—NR$^c$R$^e$, —CH(R$^c$)—NR$^c$—R$^a$—Y—R$^b$-(Z)$_x$, —CH(R)—R$^x$, —CH(R$^c$)—NR$^c$—R$^a$—C(=O)—R$^x$, and a substituent that comprises one or more phosphono groups; $R^6$ is selected from the group consisting of hydrogen, alkyl, substituted alkyl, alkenyl, substituted alkenyl, alkynyl, substituted alkynyl, —R$^a$—Y—R$^b$-(Z)$_x$, —C(O)R$^d$ and a saccharide group optionally substituted with —NR$^c$—R$^a$—Y—R$^b$-(Z)$_x$, or $R^5$ and $R^6$ can be joined, together with the atoms to which they are attached, form a heterocyclic ring optionally substituted with —NR$^c$—R$^a$—Y—R$^b$-(Z)$_x$; $R^7$ is selected from the group consisting of hydrogen, alkyl, substituted alkyl, alkenyl, substituted alkenyl, alkynyl, substituted alkynyl, —R$^a$—Y—R$^b$-(Z)$_x$, and —C(O)R$^d$; $R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; $R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; $R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —Ar$^1$—O—Ar$^2$—, where Ar$^1$ and Ar$^2$ are independently arylene or heteroarylene; $R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring; $R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, —C(NH)NR$^c$R$^c$ and —R$^a$—Y—R$^b$-(Z)$_x$, or $R^{11}$ and $R^{12}$ are joined, together with the nitrogen atom to which they are attached, to form a heterocyclic ring; $R^{13}$ is selected from the group consisting of hydrogen or —OR$^{14}$; $R^{14}$ is selected from hydrogen, —C(O)R$^d$, and a saccharide group; each $R^a$ is independently selected from the group consisting of alkylene, substituted alkylene, alkenylene, substituted alkenylene, alkynylene and substituted alkynylene; each $R^b$ is independently selected from the group consisting of a covalent bond, alkylene, substituted alkylene, alkenylene, substituted alkenylene, alkynylene and substituted alkynylene, provided $R^b$ is not a covalent bond when Z is hydrogen; each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$; each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; $R^e$ is a saccharide group; each $R^f$ is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic; $R^x$ is an N-linked amino saccharide or an N-linked heterocycle; $X^1$, $X^2$ and $X^3$ are independently selected from hydrogen or chloro; each Y is independently selected from the group consisting of oxygen, sulfur, —S—S—, —NR$^c$—, —S(O)—, —SO$_2$—, —NR$^c$C(O)—, —OSO$_2$—, —OC(O)—, —NR$^c$SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(=O)—, and —NR$^c$SO$_2$NR$^c$—; each Z is independently selected from hydrogen, aryl, cycloalkyl, cycloalkenyl, heteroaryl and heterocyclic; n is 0, 1 or 2; and x is 1 or 2; or a pharmaceutically acceptable salt, stereoisomer, or prodrug thereof; provided at least one of $R^3$ and $R^5$ is a substituent comprising one or more phosphono groups.

Preferably, $R^1$ is a saccharide group optionally substituted with —R$^a$—Y—R$^b$-(Z)$_x$, R$^f$, —C(O)R$^f$, or —C(O)—R$^a$—Y—R$^b$-(Z). More preferably $R^1$ is a saccharide group substituted on the saccharide nitrogen with —CH$_2$CH$_2$—NH—(CH$_2$)$_9$CH$_3$; —CH$_2$CH$_2$CH$_2$—NH—(CH$_2$)$_8$CH$_3$; —CH$_2$CH$_2$CH$_2$CH$_2$—NH—(CH$_2$)$_7$CH$_3$; —CH$_2$CH$_2$—NHSO$_2$—(CH$_2$)$_9$CH$_3$; —CH$_2$CH$_2$—NHSO$_2$—(CH$_2$)$_{11}$CH$_3$; —CH$_2$CH$_2$—S—(CH$_2$)$_8$CH$_3$; —CH$_2$CH$_2$—S—(CH$_2$)$_9$CH$_3$; —CH$_2$CH$_2$—S—(CH$_2$)$_{10}$CH$_3$; —CH$_2$CH$_2$CH$_2$—S—(CH$_2$)$_8$CH$_3$; —CH$_2$CH$_2$CH$_2$—S—(CH$_2$)$_9$CH$_3$; —CH$_2$CH$_2$—S—(CH$_2$)$_3$—CH═CH—(CH$_2$)$_4$CH$_3$ (trans); —CH$_2$CH$_2$CH$_2$CH$_2$—S—(CH$_2$)$_7$CH$_3$; —CH$_2$CH$_2$—S(O)—(CH$_2$)$_9$CH$_3$; —CH$_2$CH$_2$—S—(CH$_2$)$_6$Ph; —CH$_2$CH$_2$—S—(CH$_2$)$_8$Ph; —CH$_2$CH$_2$CH$_2$—S—(CH$_2$)$_8$Ph; —CH$_2$CH$_2$—NH—CH$_2$-4-(4-Cl-Ph)-Ph; —CH$_2$CH$_2$—NH—CH$_2$-4-[4-(CH$_3$)$_2$CHCH$_2$—]-Ph; —CH$_2$CH$_2$—NH—CH$_2$-4-(4-CF$_3$-Ph)-Ph; —CH$_2$CH$_2$—S—CH$_2$-4-(4-Cl-Ph)-Ph; —CH$_2$CH$_2$—S(O)—CH$_2$-4-(4-Cl-Ph)-Ph; —CH$_2$CH$_2$CH$_2$—S—CH$_2$-4-(4-Cl-Ph)-Ph; —CH$_2$CH$_2$CH$_2$—S(O)—CH$_2$-4-(4-Cl-Ph)-Ph; —CH$_2$CH$_2$CH$_2$—S—CH$_2$-4-[3,4-di-Cl-PhCH$_2$O—)-Ph; —CH$_2$CH$_2$—NHSO$_2$—CH$_2$-4-[4-(4-Ph)-Ph]-Ph; —CH$_2$CH$_2$CH$_2$—NHSO$_2$—CH$_2$-4-(4-Cl-Ph)-Ph; —CH$_2$CH$_2$CH$_2$—NHSO$_2$—CH$_2$-4-(Ph-C≡C—)-Ph; —CH$_2$CH$_2$CH$_2$—NHSO$_2$-4-(4-Cl-Ph)-Ph; or —CH$_2$CH$_2$CH$_2$—NHSO$_2$-4-(naphth-2-yl)-Ph. Preferably R$^1$ is also a saccharide group substituted on the saccharide nitrogen with a 4-(4-chlorophenyl)benzyl group or with a 4-(4-chlorobenzyloxy)benzyl group.

In a preferred embodiment, R$^1$ is a saccharide group of the formula:

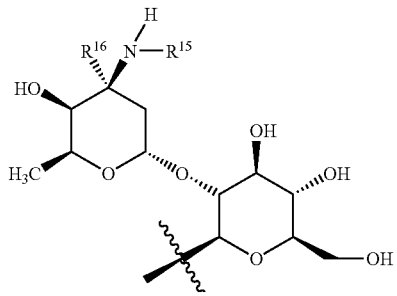

wherein R$^{15}$ is —R$^a$—Y—R$^b$-(Z)$_x$, R$^f$, —C(O)R$^f$, or —C(O)—R$^a$—Y—R$^b$-(Z)$_x$; and R$^{16}$ is hydrogen or methyl.

Preferably, R$^{15}$ is —CH$_2$CH$_2$—NH—(CH$_2$)$_9$CH$_3$; —CH$_2$CH$_2$CH$_2$—NH—(CH$_2$)$_8$CH$_3$; —CH$_2$CH$_2$CH$_2$CH$_2$—NH—(CH$_2$)$_7$CH$_3$; —CH$_2$CH$_2$—NHSO$_2$—(CH$_2$)$_9$CH$_3$; —CH$_2$CH$_2$—NHSO$_2$—(CH$_2$)$_{11}$CH$_3$; —CH$_2$CH$_2$—S—(CH$_2$)$_8$CH$_3$; —CH$_2$CH$_2$—S—(CH$_2$)$_9$CH$_3$; —CH$_2$CH$_2$—S—(CH$_2$)$_{10}$CH$_3$; —CH$_2$CH$_2$CH$_2$—S—(CH$_2$)$_8$CH$_3$; —CH$_2$CH$_2$CH$_2$—S—(CH$_2$)$_9$CH$_3$; —CH$_2$CH$_2$CH$_2$—S—(CH$_2$)$_3$—CH═CH—(CH$_2$)$_4$CH$_3$ (trans); —CH$_2$CH$_2$CH$_2$CH$_2$—S—(CH$_2$)$_7$CH$_3$; —CH$_2$CH$_2$—S(O)—(CH$_2$)$_9$CH$_3$; —CH$_2$CH$_2$—S—(CH$_2$)$_6$Ph; —CH$_2$CH$_2$—S—(CH$_2$)$_8$Ph; —CH$_2$CH$_2$CH$_2$—S—(CH$_2$)$_8$Ph; —CH$_2$CH$_2$—NH—CH$_2$-4-(4-Cl-Ph)-Ph; —CH$_2$CH$_2$—NH—CH$_2$-4-[4-(CH$_3$)$_2$CHCH$_2$-]-Ph; —CH$_2$CH$_2$—NH—CH$_2$-4-(4-CF$_3$-Ph)-Ph; —CH$_2$CH$_2$—S—CH$_2$-4-(4-Cl-Ph)-Ph; —CH$_2$CH$_2$—S(O)—CH$_2$-4-(4-Cl-Ph)-Ph; —CH$_2$CH$_2$CH$_2$—S—CH$_2$-4-(4-Cl-Ph)-Ph; —CH$_2$CH$_2$CH$_2$—S(O)—CH$_2$-4-(4-Cl-Ph)-Ph; —CH$_2$CH$_2$CH$_2$—S—CH$_2$-4-[3,4-di-Cl-PhCH$_2$O—)-Ph; —CH$_2$CH$_2$—NHSO$_2$—CH$_2$-4-[4-(4-Ph)-Ph]-Ph; —CH$_2$CH$_2$CH$_2$—NHSO$_2$—CH$_2$-4-(4-Cl-Ph)-Ph; —CH$_2$CH$_2$CH$_2$—NHSO$_2$—CH$_2$-4-(Ph-C≡C—)-Ph; —CH$_2$CH$_2$CH$_2$—NHSO$_2$-4-(4-Cl-Ph)-Ph; or —CH$_2$CH$_2$CH$_2$—NHSO$_2$-4-(naphth-2-yl)-Ph. Preferably R$^{15}$ can also be a 4-(4-chlorophenyl)benzyl group or a 4-(4-chlorobenzyloxy)benzyl group.

Preferably, R$^2$ is hydrogen.

Preferably, R$^3$ is —OR$^c$; —NR$^c$R$^c$; or a nitrogen-linked, oxygen-linked, or sulfur-linked substituent comprising one or two phosphono groups, or a pharmaceutically acceptable salt thereof. When R$^3$ is a phosphono-containing substituent, R$^3$ is preferably a nitrogen-linked substituent comprising one phosphono group, or a pharmaceutically acceptable salt thereof. Preferably, R$^3$ is a group of the formula —O—R$^a$—P(O)(OH)$_2$, —S—R$^a$—P(O)(OH)$_2$, or —NR$^c$—R$^a$—P(O)(OH)$_2$. More preferably, R$^3$ is a group of the formula —NH—R$^a$—P(O)(OH)$_2$, where R$^a$ is as defined herein. In this formula, R$^a$ is preferably an alkylene group. Particularly preferred R$^3$ substituents include phosphonomethylamino, 3-phosphonopropylamino and 2-hydroxy-2-phosphonoethylamino groups and the like.

Preferably, when R$^3$ is not a phosphono-containing substituent, R$^3$ is —OH; —NH—(CH$_2$)$_3$—N(CH$_3$)$_2$; N-(D-glucosamine); —NHCH(CO$_2$CH$_3$)CH$_2$CO$_2$CH$_3$; —NH(CH$_2$)$_3$-(morpholin-4-yl); —NH(CH$_2$)$_3$—NH(CH$_2$)$_2$CH$_3$; —NH(CH$_2$-piperidin-1-yl; —NH(CH$_2$)$_4$NHC(N)NH$_2$; —NH(CH$_2$)$_2$—N$^+$(CH$_3$)$_3$; —NHCH(COOH)(CH$_2$)$_3$NHC(N)NH$_2$; —NH—[CH$_2$CH$_2$CH$_2$—NH—]3-H; —N[(CH$_2$)$_3$N(CH$_3$)$_2$]$_2$; —NH(CH$_2$)$_3$-imidazol-1-yl; —NHCH$_2$-4-pyridyl; —NH(CH$_2$)$_3$CH$_3$; —NH(CH$_2$)$_2$OH; —NH(CH$_2$)$_5$OH; —NH(CH$_2$)$_2$OCH$_3$; —NHCH$_2$-tetrahydrofuran-2-yl; —N[(CH$_2$)$_2$OH]$_2$; —NH(CH$_2$)$_2$N[(CH$_2$)$_2$OH]$_2$; —NHCH$_2$COOH; —NHCH(COOH)CH$_2$OH; —NH(CH$_2$)$_2$COOH; N-(glucamine); —NH(CH$_2$)$_2$COOH; —NH(CH$_2$)$_3$SO$_3$H; —NHCH(COOH)(CH$_2$)$_2$NH$_2$; —NHCH(COOH)(CH$_2$)$_3$NH$_2$; —NHCH(COOH)CH$_2$CO$_2$(CH$_2$)$_3$—N$^+$(CH$_3$)$_3$; —NHCH(COOH)CH$_2$CO$_2$(CH$_2$)$_2$C(O)—N(CH$_3$)$_2$; —NHCH(COOH)CH$_2$CO$_2$(CH$_2$)$_3$-morpholin4-yl; —NHCH(COOH)CH$_2$CO$_2$(CH$_2$)$_2$OC(O)C(CH$_3$)$_3$; —NHCH(CH$_2$COOH)CO$_2$(CH$_2$)$_3$—N$^+$(CH$_3$)$_3$; —NHCH(CH$_2$COOH)CO$_2$(CH$_2$)2C(O)N(CH$_3$)$_2$; or —NHCH(CH$_2$COOH)CO$_2$(CH$_2$)$_3$-morpholin-4-yl. —NHCH(CH$_2$COOH)CO$_2$(CH$_2$)$_2$OC(O)C(CH$_3$)$_3$; —NHCH(COOH)CH$_2$CO$_2$CH$_3$; —NHCH(CH$_2$COOH)CO$_2$(CH$_2$)$_2$N(CH$_3$)$_2$; —NHCH(COOH)CH$_2$CO$_2$CH$_2$C(O)N(CH$_3$)$_2$; —NHCH(CH$_2$COOH)CO$_2$CH$_2$C(O)N(CH$_3$)$_2$; —NHCH(CH$_2$COOH)CO$_2$CH$_3$; —NH(CH$_2$)$_3$N(CH$_3$)$_2$; —NHCH$_2$CH$_2$CO$_2$CH$_3$; —NHCH[CH$_2$CO$_2$CH$_2$C(O)N(CH$_3$)$_2$]CO$_2$CH$_2$—C(O)—N(CH$_3$)$_2$; —NHCH$_2$CO$_2$CH$_3$; —N-(methyl 3-amino-3-deoxyaminopyranoside); —N-(methyl 3-amino-2,3,6-trideoxyhexopyranoside); —N-(2-amino-2-deoxy-6-(dihydrogenphosphate)glucopyranose; —N-(2-amino-2-deoxygluconic acid); —NH(CH$_2$)$_4$COOH; —N—N—CH$_3$-D-glucamine; —NH(CH$_2$)$_6$COOH; —O(D-glucose); —NH(CH$_2$)$_3$OC(O)CH(NH$_2$)CH$_3$; —NH(CH$_2$)$_4$CH(C(O)-2-HOOC-pyrrolidin-1-yl)NHCH(COOH)—CH$_2$CH$_2$Ph (S,S isomer); —NH—CH$_2$CH$_2$—NH—(CH$_2$)$_9$CH$_3$; —NH(CH$_2$)C(O)CH$_2$C(O)N(CH$_3$)$_2$;

Preferably, R$^4$, R$^6$ and R$^7$ are each independently selected from hydrogen or —C(O)R$^d$. More preferably, R$^4$, R$^6$ and R$^7$ are each hydrogen.

Preferably, R$^5$ is hydrogen, —CH$_2$—NHR$^c$, —CH$_2$—NR$^c$R$^e$, —CH$_2$—NH—R$^a$—Y—R$^b$-(Z)$_x$, or a substituent comprising one or two phosphono groups. When R$^5$ is a substituent comprising a phosphono group, R$^5$ is preferably a group of the formula —CH($^{21}$)—N(R$^c$)—R$^a$—P(O)(OH)$_2$ wherein R$^{21}$ is hydrogen or R$^d$, preferably hydrogen, and R$^a$, R$^c$, and R$^d$, are as defined herein. More preferably, when R$^5$ is phosphono-containing substituent, R$^5$ is preferably a group of the formula —CH$_2$—NH—R$^a$—P(O)(OH)$_2$, where R$^a$ is as defined herein. In this formula, R$^a$ is preferably an alkylene group; more preferably, an alkylene group containing from 2 to about 6 carbon atoms.

Particularly preferred R⁵ substituents include N-(phosphonomethyl)-aminomethyl; N-(2-hydroxy-2-phosphonoethyl)aminomethyl; N-carboxymethyl-N-(2-phosphonoethyl)aminomethyl; N,N-bis(phosphonomethyl)-aminomethyl; and N-(3-phosphonopropyl)aminomethyl; and the like.

Preferably, when R⁵ is not a phosphono-containing Substituent, R⁵ is hydrogen, —CH₂—NHR$^c$, —CH₂—NR$^c$R$^e$ or —CH₂—NH—R$^a$—Y—R$^b$-(Z)$_x$. R⁵ can also preferably be hydrogen; —CH₂-N-(N-CH₃-D-glucamine); —CH₂—NH—CH₂CH₂—NH—(CH₂)₉CH₃; —CH₂—NH—CH₂CH₂—NHC(O)—(CH₂)₃COOH; —CH₂—NH—(CH₂)₉ CH₃; —CH₂—NH—CH₂CH₂—COOH; —CH₂—NH—(CH₂)₅COOH; —CH₂-(morpholin-4-yl); —CH₂—NH—CH₂CH₂—O—CH₂CH₂OH; —CH₂—NH—CH₂CH(OH)—CH₂OH; —CH₂—N[CH₂CH₂OH]₂; —CH₂—NH—(CH₂)₃—N(CH₃)₂; —CH₂—N[(CH₂)₃—N(CH₃)₂]₂; —CH₂—NH—(CH₂)₃-(imidazol-1-yl); —CH₂—NH—(CH₂)₃-(morpholin-4-yl); —CH₂—NH—(CH₂)₄—NHC(NH)NH₂; —CH₂-N-(2-amino-2-deoxygluconic acid); —CH₂—NH—CH₂CH₂—NH—(CH₂)₁₁CH₃; —CH₂—NH—CH(COOH)CH₂COOH; —CH₂—NH—CH₂CH₂—NHSO₂—(CH₂)₇CH₃; —CH₂—NH—CH₂CH₂—NHSO₂—(CH₂)₈CH₃; —CH₂—NH—CH₂CH₂—NHSO₂—(CH₂)₉CH₃; —CH₂—NH—CH₂CH₂—NHSO₂—(CH₂)₁₁CH₃; —CH₂—NH—CH₂CH₂—NH—(CH₂)₇CH₃; —CH₂—NH—CH₂CH₂—O—CH₂CH₂OH; —CH₂—NH—CH₂CH₂C(O)-N-(D-glucosamine); —CH₂—NH-(6-oxo-[1,3]oxazinan-3-yl); —CH₂—NH—CH₂CH₂—S—(CH₂)₇CH₃; —CH₂—NH—CH₂CH₂—S—(CH₂)₈CH₃; —CH₂—NH—CH₂CH₂—S—(CH₂)₉CH₃; —CH₂—NH—CH₂CH₂—S—CH₂)₁₁CH₃; —CH₂—NH—CH₂CH₂—S—(CH₂)₆Ph; —CH₂—NH—CH₂CH₂—S—(CH₂)₈Ph; —CH₂—NH—CH₂CH₂—S—(CH₂)₁₀Ph; —CH₂—NH—CH₂CH₂—S—CH₂-(4-(4-CF₃-Ph)Ph); —CH₂—NH—CH₂CH₂—NH—(CH₂)₁₁CH₃; or —CH₂—NH—(CH₂)₅—COOH.

Preferably, R⁸ is —CH₂C(O)NH₂, —CH₂COOH, benzyl, 4-hydroxyphenyl or 3-chloro-4-hydroxyphenyl.

Preferably, R⁹ is hydrogen or alkyl.

Preferably, R¹⁰ is alkyl or substituted alkyl. More preferably, R¹⁰ is the side-chain of a naturally occurring amino acid, such as isobutyl.

Preferably, R¹¹ is hydrogen or alkyl.

Preferably, R¹² is hydrogen, alkyl, substituted alkyl or —C(O)R$^d$. R¹² can also preferably be hydrogen; —CH₂COOH; —CH₂—[CH(OH)]₅CH₂OH; —CH₂CH(OH)CH₂OH;—CH₂CH₂NH₂; —CH₂C(O)OCH₂CH₃; —CH₂-(2-pyridyl); —CH₂—[CH(OH)]₄COOH; —CH₂-(3-carboxyphenyl); (R)—C(O)CH(NH₂)(CH₂)₄NH₂; —C(O)Ph; —C(O)CH₂NHC(O)CH₃; E-CH₂CH₂—S—(CH₂)₃CH=CH(CH₂)₄CH₃; or —C(O)CH₃.

Preferably, X¹ and X² are each chloro.

Preferably, X³ is hydrogen.

Preferably, each Y is independently selected from the group consisting of oxygen, sulfur, —S—S—, —NR$^c$—, —S(O)—, —SO₂—, —NR$^c$C(O)—, —OSO₂—, —OC(O)—, —NR$^c$SO₂—, —C(O)NR$^c$, —C(O)O—, —SO₂NR$^c$—, —SO₂O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, and —NR$^c$SO₂NR$^c$—.

Preferably, n is 0 or 1, and more preferably, n is 1.

Another preferred compound of the invention is a glycopeptide of formula II:

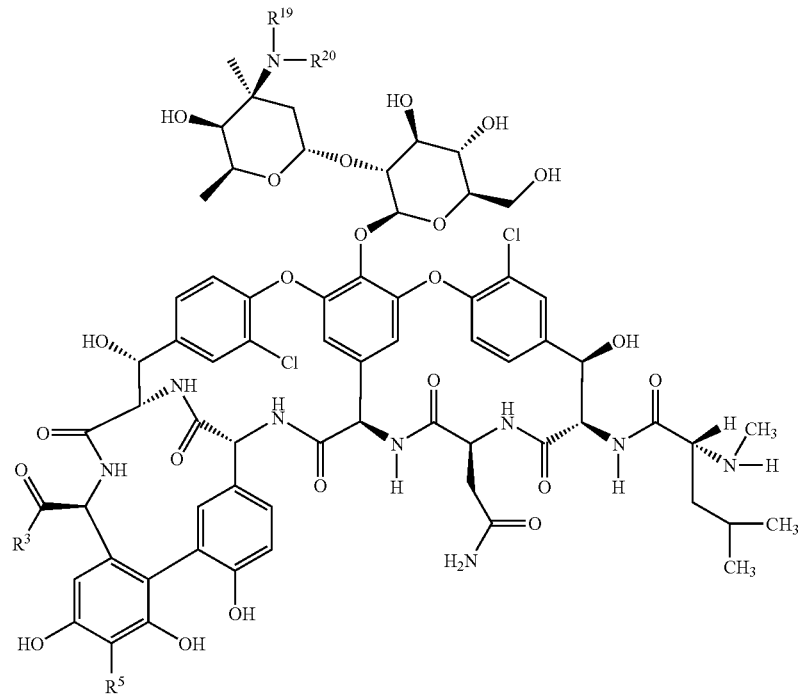

(II)

wherein:

$R^{19}$ is hydrogen;

$R^{20}$ is —$R^a$—Y—$R^b$-(Z)$_x$, $R^f$, —C(O)$R^f$, or —C(O)—$R^a$—Y—$R^b$-(Z)$_x$; and $R^a$, Y, $R^b$, Z, x, $R^f$, $R^3$, and $R^5$ have any of the values or preferred values described herein;

or a pharmaceutically acceptable salt, stereoisomer, or prodrug thereof;

provided at least one of $R^3$ and $R^5$ is a substituent comprising one or more phosphono groups.

Preferably, $R^{20}$ is —CH$_2$CH$_2$—NH—(CH$_2$)$_9$CH$_3$; —CH$_2$CH$_2$—NH—(CH$_2$)$_8$CH$_3$; —CH$_2$CH$_2$CH$_2$—NH—(CH$_2$)$_7$CH$_3$; —CH$_2$CH$_2$—NHSO$_2$—(CH$_2$)$_9$CH$_3$; —CH$_2$CH$_2$—NHSO$_2$—(CH$_2$)$_{11}$CH$_3$; —CH$_2$CH$_2$—S—(CH$_2$)$_8$CH$_3$; —CH$_2$CH$_2$—S—(CH$_2$)$_9$CH$_3$; —CH$_2$CH$_2$—S—(CH$_2$)$_{10}$CH$_3$; —CH$_2$CH$_2$CH$_2$—S—(CH$_2$)$_8$CH$_3$; —CH$_2$CH$_2$CH$_2$—S—(CH$_2$)$_9$CH$_3$; —CH$_2$CH$_2$—S—(CH$_2$)$_3$—CH=CH—(CH$_2$)$_4$CH$_3$ (trans); —CH$_2$CH$_2$CH$_2$—S—(CH$_2$)$_7$CH$_3$; —CH$_2$CH$_2$—S(O)—(CH$_2$)$_9$CH$_3$; —CH$_2$CH$_2$—S—(CH$_2$)$_6$Ph; —CH$_2$CH$_2$—S—(CH$_2$)$_8$Ph; —CH$_2$CH$_2$CH$_2$—S—(CH$_2$)$_8$Ph; —CH$_2$CH$_2$—NH—CH$_2$-4-(4-Cl-Ph)-Ph; —CH$_2$CH$_2$—NH—CH$_2$-4-[4-(CH$_3$)$_2$CHCH$_2$—]-Ph; —CH$_2$CH$_2$—NH—CH$_2$-4-(4-CF$_3$-Ph)-Ph; —CH$_2$CH$_2$—S—CH$_2$-4-(4-Cl-Ph)-Ph; —CH$_2$CH$_2$—S(O)—CH$_2$-4-(4-Cl-Ph)-Ph; —CH$_2$CH$_2$CH$_2$—S—CH$_2$-4-(4-Cl-Ph)-Ph; —CH$_2$CH$_2$CH$_2$—S(O)—CH$_2$-4-(4-Cl-Ph)-Ph; —CH$_2$CH$_2$CH$_2$—S—CH$_2$-4-[3,4-di-Cl-PhCH$_2$O—)-Ph; —CH$_2$CH$_2$—NHSO$_2$—CH$_2$-4-[4-(4-Ph)-Ph]-Ph; —CH$_2$CH$_2$CH$_2$—NHSO$_2$—CH$_2$-4-(4-Cl-Ph)-Ph; —CH$_2$CH$_2$CH$_2$—NHSO$_2$—CH$_2$-4-(Ph-C≡C—)-Ph; —CH$_2$CH$_2$CH$_2$—NHSO$_2$-4-(4-Cl-Ph)-Ph; or —CH$_2$CH$_2$CH$_2$—NHSO$_2$-4-(naphth-2-yl)-Ph. Preferably $R^{20}$ is also a 4-(4-chlorophenyl)benzyl group or a 4-(4-chlorobenzyloxy)benzyl group.

In another preferred embodiment, the invention provides a compound of formula II, wherein $R^{19}$ is hydrogen; $R^{20}$ is —CH$_2$CH$_2$NH—(CH$_2$)$_9$CH$_3$; $R^3$ is —OH; and $R^5$ is a substituent comprising a phosphono group; or a pharmaceutically acceptable salt thereof.

In yet another preferred embodiment, the invention provides a compound of formula II, wherein $R^{19}$ is hydrogen; $R^{20}$ is —$R^a$—Y—$R^b$-(Z)$_x$, $R^f$, —C(O)$R^f$, or —C(O)—$R^a$—Y—$R^b$-(Z)$_x$; $R^3$ is —OH; and $R^5$ is —CH$_2$—NH—$R^a$—P(O)(OH)$_2$; or a pharmaceutically acceptable salt thereof.

The invention also provides a pharmaceutical composition comprising a pharmaceutically acceptable carrier and a therapeutically effective amount of a compound of the invention. In one preferred embodiment, the pharmaceutically acceptable carrier comprises an aqueous cyclodextrin solution. Preferably, the cyclodextrin is hydroxypropyl-β-cyclodextrin or sulfobutyl ether β-cyclodextrin. More preferably, the cyclodextrin is hydroxypropyl-β-cyclodextrin.

The compounds of the invention are highly effective antibacterial agents. Accordingly, the invention also provides a method of treating a mammal having a bacterial disease, comprising administering to the mammal a therapeutically effective amount of a compound of the invention. The invention also provides a method of treating a mammal having a bacterial disease, comprising administering to the mammal a therapeutically effective amount of a pharmaceutical composition of the invention.

The invention also provides processes and intermediates useful for preparing compounds of the invention, which processes and intermediates are described further herein.

The invention also provides a compound of the invention as described herein for use in medical therapy, as well as the use of a compound of the invention in the manufacture of a formulation or medicament for treating a bacterial disease in a mammal.

The invention also provides a pharmaceutical composition which comprises as an active ingredient a compound of the invention for the treatment of a bacterial disease.

The invention also provides a method for preparing a glycopeptide of the invention which is substituted at the C-terminus with a substituent that comprises one or more phosphono groups, comprising coupling a corresponding starting glycopeptide wherein the C-terminus is a carboxy group with a suitable phosphono containing compound.

The invention also provides a method for preparing a glycopeptide of the invention which is substituted at the R-terminus with a substituent that comprises one or more phosphono groups, comprising coupling a corresponding starting glycopeptide wherein the R-terminus is unsubstituted with a suitable phosphono containing compound. When the starting glycopeptide is substituted at the vancosamine amino terminus, such a method can further optionally comprise preparing the starting glycopeptide by reductively alkylating a corresponding glycopeptide wherein the vancosamine amino terminus is the corresponding amine.

The invention also provides a method for preparing a glycopeptide of the invention that is substituted at the C-terminus, comprising derivatizing a corresponding starting glycopeptide wherein the C-terminus is a carboxy group.

The invention also provides a method for preparing a glycopeptide of the invention which is substituted at the R-terminus, comprising derivatizing a corresponding starting glycopeptide wherein the R-terminus is unsubstituted (i.e. a hydrogen).

This invention also provides a method for preparing a compound of formula II, wherein $R^3$ is —OH, $R^5$ is —CH$_2$—NH—$R^a$—P(O)(OH)$_2$, $R^{19}$ is hydrogen and $R^{20}$ is —$R^a$—Y—$R^b$-(Z)$_x$ or —$R^f$, and $R^a$, $R^b$, $R^f$, Y, Z and x are as defined herein, or salt thereof; the method comprising:

(a) reductively alkylating a compound of formula II, wherein $R^3$ is —OH and $R^5$, $R^{19}$ and $R^{20}$ are hydrogen, or a salt thereof, with an aldehyde of the formula HC(O)—$R^{a'}$—Y—$R^b$-(Z)$_x$ or HC(O)$R^{f'}$ wherein $R^{a'}$ and $R^{f'}$ represent $R^a$ and $R^f$, respectively, minus one —CH$_2$— group, to form a compound of formula II wherein $R^3$ is —OH, $R^5$ and $R^{19}$ are hydrogen and $R^{20}$ is —$R^a$—Y—$R^b$-(Z)$_x$ or —$R^f$, or salt thereof; and (b) reacting the product from step (a) with formaldehyde and H$_2$N—$R^a$—P(O)(OH)$_2$ to form a compound of formula II wherein $R^3$ is —OH, $R^5$ is —CH$_2$NH—$R^a$—P(O)(OH)$_2$, $R^{19}$ is hydrogen and $R^{20}$ is —$R^a$—Y—$R^b$-(Z)$_x$ or —$R^f$, or salt thereof.

Preferred compounds of the invention are the compounds of formula II shown in Table I below wherein $R^{19}$ is hydrogen.

TABLE I

Preferred Compounds of formula II

| Compound | $R^3$ | $R^5$ | $R^{20}$ |
|---|---|---|---|
| 1 | phosphonomethylamino | H | CH$_3$(CH$_2$)$_9$NHCH$_2$CH$_2$— |
| 2 | phosphonomethylamino | H | CH$_3$(CH$_2$)$_9$OCH$_2$CH$_2$— |
| 3 | phosphonomethylamino | H | CH$_3$(CH$_2$)$_9$SCH$_2$CH$_2$— |

TABLE I-continued

Preferred Compounds of formula II

| Compound | $R^3$ | $R^5$ | $R^{20}$ |
|---|---|---|---|
| 4 | phosphonomethylamino | H | $CH_3(CH_2)_{12}$— |
| 5 | phosphonomethylamino | H | 4-(4-chlorophenyl)-benzyl |
| 6 | phosphonomethylamino | H | 2-(4-(4-chlorophenyl)-benzylamino)ethyl |
| 7 | phosphonomethylamino | H | 4-(4'-chlorobiphenyl)-butyl |
| 8 | phosphonomethylamino | H | 5-(4'-chlorobiphenyl)-pentyl |
| 9 | 3-phosphonopropylamino | H | $CH_3(CH_2)_9SCH_2CH_2$— |
| 10 | 2-hydroxy-2-phosphonoethylamino | H | 4-(4-chlorophenyl)-benzyl |
| 11 | OH | (phosphonomethyl)-aminomethyl | $CH_3(CH_2)_9NHCH_2CH_2$— |
| 12 | OH | (phosphonomethyl)-aminomethyl | $CH_3(CH_2)_9SCH_2CH_2$— |
| 13 | OH | (phosphonomethyl)-aminomethyl | $CH_3(CH_2)_9OCH_2CH_2$— |
| 14 | OH | (phosphonomethyl)-aminomethyl | $CH_3(CH_2)_{12}$— |
| 15 | OH | (phosphonomethyl)-aminomethyl | 4-(4-chlorophenyl)benzyl |
| 16 | OH | (phosphonomethyl)-aminomethyl | 2-(4-(4-chlorophenyl)-benzylamino)ethyl |
| 17 | OH | (phosphonomethyl)-aminomethyl | 4-(4'-chlorobiphenyl)butyl |
| 18 | OH | (phosphonomethyl)-aminomethyl | 5-(4'-chlorobiphenyl)pentyl |
| 19 | OH | (phosphonomethyl)-aminomethyl | 3-[4-(4-chlorobenzyloxy)-benzylthio]propyl |
| 20 | OH | N-(2-hydroxy-2-phosphonoethyl)aminomethyl | $CH_3(CH_2)_9SCH_2CH_2$— |
| 21 | OH | N-(carboxymethyl)-N-2-phosphonomethyl)-aminomethyl | $CH_3(CH_2)_9SCH_2CH_2$— |
| 22 | OH | N,N-bis(phosphonomethyl)aminomethyl | $CH_3(CH_2)_9NHCH_2CH_2$— |
| 23 | OH | 3-phosphonopropyl-aminomethyl | $CH_3(CH_2)_9SCH_2CH_2$— |
| 24 | OH | 3-phosphonopropyl-aminomethyl | 4-(4-chlorophenyl)benzyl |
| 25 | phosphonomethylamino | —$CH_2$—N—(N—$CH_3$—D-glucamine | $CH_3(CH_2)_9NHCH_2CH_2$— |
| 26 | OH | (phosphonomethyl)-aminomethyl | —$(CH_2)_3NH$—$SO_2$-4-(4-chlorophenyl)phenyl |

Another preferred group of compounds of the invention are phosphono derivatives of the glycopeptide antibiotic A82846B (also known as chloroorienticin A oy LY264826). See for example R. Nagarajan et al., *J. Org. Chem.*, 1988, 54, 983–986; and N. Tsuji et al., *J. Antibiot.*, 1988, 41, 819–822. The structure of this glycopeptide is similar to vancomycin, except A82846B contains an additional amino sugar (i.e. 4-epi-vancosamine attached at the $R^2$ position in formula I) and further contains 4-epi-vancosamine in place of vancosamine in the disaccharide moiety attached at the $R^1$ position in formula I. For example, a preferred group of compounds are N-alkylated derivatives of A82846B that are substituted at the C-terminus or the R-terminus with a substituent that comprises one or more (e.g. 1, 2, 3, 4, or 5) phosphono (—$PO_3H_2$) groups; or a pharmaceutically acceptable salt thereof. A preferred group of compounds of the invention that are derivatives of A82846B are substituted at either the C-terminus or the R-terminus with a substituent that comprises one or more (e.g. 1, 2, 3, 4, or 5) phosphono (—$PO_3H_2$) groups. Another preferred group of compounds of the invention that are derivatives of A82846B are substituted at the C-terminus and the R-terminus with substituents that each comprises one or more (e.g. 1, 2, 3, 4, or 5) phosphono (—$PO_3H_2$) groups. Another preferred group of compounds of the invention are phosphono derivatives of A82846B having a 4-(4-chlorophenyl)benzyl group or a 4-(4-chlorobenzyloxy)benzyl group attached at the amino group of the 4-epi-vancosamine of the disaccharide moiety. The compounds of the invention that are phosphono derivatives of A82846B can readily be prepared using the procedures described herein.

The phosphono compounds of the invention have been found to unexpectedly exhibit reduced tissue accumulation and/or nephrotoxicity when administered to a mammal. While not wishing to be bound by theory, it is believed that the phosphono moiety serves to increase the overall negative charge of the glycopeptide under physiological conditions thereby facilitating excretion from the mammal after administration. The unexpected increase in excretion of the phosphono compounds of the invention may be responsible for the reduced tissue accumulation and/or reduced nephrotoxicity observed for these compounds relative to the corresponding compounds that lack the phosphono functionality.

DETAILED DESCRIPTION OF THE INVENTION

This invention relates to novel compounds of the invention, which are derivatives of glycopeptide antibiotics comprising one or more substituents that comprise one or more phosphono groups, as well as to compositions comprising such compounds and to therapeutic methods comprising the administration of such compounds. When describing the compounds, compositions and methods of the invention, the following terms have the following meanings, unless otherwise indicated.

Definitions

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 8 substituents, preferably 1 to 5 substituents, and more preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_3$H, guanido, and —SO$_2$-heteroaryl.

The term "alkylene" refers to a diradical of a branched or unbranched saturated hydrocarbon chain, preferably having from 1 to 40 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures. Additionally, the term substituted alkylene includes alkylene groups in which from 1 to 5 of the alkylene carbon atoms are replaced with oxygen, sulfur or —NR— where R is hydrogen or alkyl. Examples of substituted alkylenes are chloromethylene (—CH(Cl)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—) and the like.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alky, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH═CH$_2$), n-propenyl (—CH$_2$CH═CH$_2$); iso-propenyl (—C(CH$_3$)═CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "arninocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, sulfonamide, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

"Amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

The term "carboxy" refers to —COOH.

The term "C-terminus" as it relates to a glycopeptide is well understood in the art. For example, for a glycopeptide of formula 1, the C-terminus is the position substituted by the group $R^3$.

The term "dicarboxy-substituted alkyl" refers to an alkyl group substituted with two carboxy groups. This term includes, by way of example, —$CH_2$(COOH)$CH_2$COOH and —$CH_2$(COOH)$CH_2CH_2$COOH.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "halo" or "halogen" refers to fluoro, chloro, bromo and iodo. "Haloalkyl" refers to alkyl as defined herein substituted by 14 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroarylalkyl" refers to (heteroaryl)alkyl- where heteroaryl and alkyl are as defined herein. Representative examples include 2-pyridylmethyl and the like.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, oxo (=O), and —$SO_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as "crown compounds" which refers to a specific class of heterocyclic compounds having one or more repeating units of the formula [—(CH$_2$—)$_a$A-] where a is equal to or greater than 2, and A at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocyclic-S—.

The term "N-terminus" as it relates to a glycopeptide is well understood in the art. For example, for a glycopeptide of formula II, the N-terminus is the position substituted by the group $R^{19}$ and $R^{20}$.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "phosphono" refers to —PO$_3$H$_2$.

The term "phosphonomethylamino" refers to —NH—CH$_2$—P(O)(OH)$_2$.

The term "phosphonomethylaminomethyl" refers to —CH$_2$—NH—CH$_2$—P(O)(OH)$_2$.

The term "prodrug" is well understood in the art and includes compounds that are converted to pharmaceutically active compounds of the invention in a mammalian system. For example, see *Remington's Pharmaceutical Sciences*, 1980, vol 16, Mack Publishing Company, Easton, Pa., 61 and 424.

The term "R-terminus" as it relates to a glycopeptide is well understood in the art. For example, for a glycopeptide of formula I, the R-terminus is the position substituted by the group $R^5$.

The term "saccharide group" refers to an oxidized, reduced or substituted saccharide monoradical covalently attached to the glycopeptide or other compound via any atom of the saccharide moiety, preferably via the aglycone carbon atom. The term includes amino-containing saccharide groups. Representative saccharide include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. For the purposes of this definition, these saccharide are referenced using conventional three letter nomenclature and the saccharide can be either in their open or preferably in their pyranose form.

The term "amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

The term "spiro-attached cycloalkyl group" refers to a cycloalkyl group attached to another ring via one carbon atom common to both rings.

The term "stereoisomer" as it relates to a given compound is well understood in the art, and refers another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, *Morrison and Boyde Organic Chemistry*, 1983, 4th ed., Allyn and Bacon, Inc., Boston, Mass., page 123.

The term "sulfonamide" refers to a group of the formula —SO$_2$NRR, where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

The term "thioether derivatives" when used to refer to the glycopeptide compounds of this invention includes thioethers (—S—), sulfoxides (—SO—) and sulfones (—SO$_2$—).

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Cyclodextrin" includes cyclic molecules containing six or more α-D-glucopyranose units linked at the 1,4 positions by a linkages as in amylose. β-Cyclodextrin or cycloheptaamylose contains seven α-D-glucopyranose units. As used herein, the term "cyclodextrin" also includes cyclodextrin derivatives such as hydroxypropyl and sulfobutyl ether cyclodextrins. Such derivatives are described for example, in U.S. Pat. Nos. 4,727,064 and 5,376,645. One preferred cyclodextrin is hydroxypropyl β-cyclodextrin having a degree of substitution of from about 4.1–5.1 as measured by FTIR. Such a cyclodextrin is available from Cerestar (Hammond, Ind., USA) under the name Cavitronm™ 82003.

"Glycopeptide" refers to oligopeptide (e.g. heptapeptide) antibiotics (dalbaheptides), characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences"Volume 63, edited by Ramakrishnan Nagarajan, published by Marcal Dekker, Inc.). Additional examples of glycopeptodes are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.,* 1996, 118, 13107–13108; *J. Amer. Chem. Soc.,* 1997, 119, 12041–12047; and *J. Amer. Chem. Soc.,* 1994, 116,4573–4590. Representative glycopeptides include those identified as A477, A35512, A40926, A41030, A42867, A47934, A80407, A82846, A83850 , A84575, AB-65, Actaplanin, Actinoidin, Ardacin, Avoparcin, Azureomycin, Balhimycin, Chloroorientiein, Chloropolysporin, Decaplanin, N-demethylvancomycin, Eremomycin, Galacardin, Helvecardin, Izupeptin, Kibdelin, LL-AM374, Mannopeptin, MM45289, MM47756, MM4776 1, MM4972 1, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-72051, Vancomycin, and the like. The term "glycopeptide" as used herein is also intended to include the general class of peptides disclosed above on which the sugar moiety is absent, i.e. the aglycone series of glycopeptides. For example, removal of the disaccharide moiety appended to the phenol on vancomycin by mild hydrolysis gives vancomycin aglycone. Also within the scope of the invention are glycopeptides that have been further appended with additional saccharide residues, especially aminoglycosides, in a manner similar to vancosamine.

"Optional" or "optionally" means that the subsequently described event or circumstance may or may not occur, and that the description includes instances where said event or circumstance occurs and instances in which it does not. For example, "optionally substituted" means that a group may or may not be substituted with the described substituent.

As used herein, the terms "inert organic solvent" or "inert solvent" or "inert diluent" mean a solvent or diluent which is essentially inert under the conditions of the reaction in which it is employed as a solvent or diluent. Representative examples of materials which may be used as inert solvents or diluents include, by way of illlustration, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The term "nitrogen-linked" or "N-linked" means a group or substituent is attached to the remainder of a compound (e.g. a compound of formula I) through a bond to a nitrogen of the group or substituent. The term "oxygen-linked" means a group or substituent is attached to the remainder of a compound (e.g. a compound of formula I) through a bond to an oxygen of the group or substituent. The term "sulfur-linked" means a group or substituent is attached to the remainder of a compound (e.g. a compound of formula I) through a bond to a sulfur of the group or substituent.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl anine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of this invention typically contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

The term "treatment" as used herein includes any treatment of a condition or disease in an animal, particularly a mammal, more particularly a human, and includes:

(i) preventing the disease or condition from occurring in a subject which may be predisposed to the disease but has not yet been diagnosed as having it;

(ii) inhibiting the disease or condition, i.e. arresting its development; relieving the disease or condition, i.e. causing regression of the condition; or relieving the conditions caused by the disease, i.e. symptoms of the disease.

The term "disease state which is alleviated by treatment with a broad spectrum antibacterial" or "bacterial disease" as used herein is intended to cover all disease states which are generally acknowledged in the art to be usefully treated with a broad spectrum antibacterial in general, and those disease states which have been found to be usefully treated by the specific antibacterials of this invention. Such disease states include, but are not limited to, treatment of a mammal afflicted with pathogenic bacteria, in particular staphylococci (methicillin sensitive and resistant), streptococci (penicillin sensitive and resistant), enterococci (vancomycin sensitive and resistant), and Clostridium difficile.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

The term "protecting group" or "blocking group" refers to any group which, when bound to one or more hydroxyl, thiol, amino, carboxy or other groups of the compounds, prevents undesired reactions from occurring at these groups and which protecting group can be removed by conventional chemical or enzymatic steps to reestablish the hydroxyl, thio, amino, carboxy or other group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" $3^{rd}$ Ed., 1999, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxy protecting groups include esters such as methyl, ethyl, propyl, t-butyl etc. which can be removed by mild conditions compatible with the nature of the product.

"Vancomycin" refers to a glycopeptide antibiotic having the formula:

When describing vancomycin derivatives, the term "$N^{van}$—" indicates that a substituent is covalently attached to the amino group of the vacosamine moiety of vacomycin. Similarly, the term "$N^{leu}$—" indicates that a substituent is covalently attached to the amino group of the leucine moiety of vancomycin.

General Synthetic Procedures

The glycopeptide compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis,* Third Edition, Wiley, New York, 1999, and references cited therein.

In the following reaction schemes, the glycopeptide compounds are depicted in a simplified form as a box "G" that shows the carboxy terminus labeled [C], the vancosamine amino terminus labeled [V], the "non-saccharide" amino

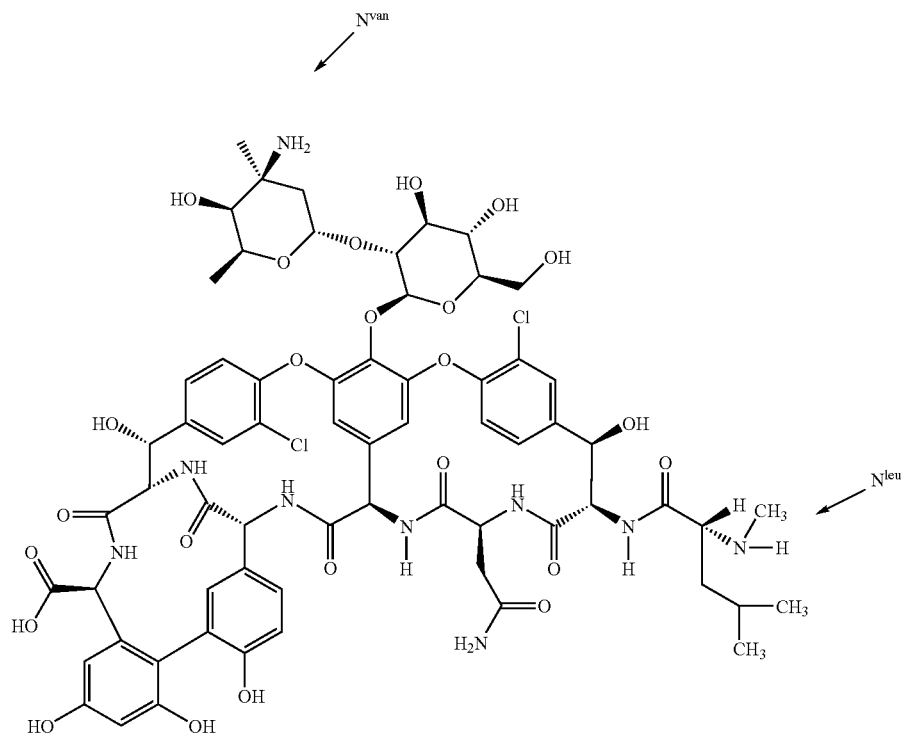

terminus (leucine amine moiety) labeled [N], and optionally, the resorcinol moiety labeled [R] as follows:

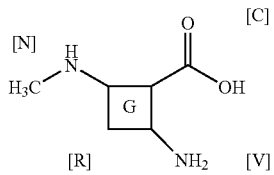

A glycopeptide compound of the present invention, which is substituted at the C-terminus with a substituent that comprises one or more (e.g. 1, 2, 3, 4, or 5) phosphono (—PO$_3$H$_2$) groups, can be prepared by coupling a corresponding glycopeptide compound wherein the C-terminus is a carboxy group with a suitable phosphono containing compound. For example, a glycopeptide compound wherein the C-terminus is a carboxy group can be coupled with a phosphono containing amine, alcohol, or thiol compound to form an amide, an ester, or a thioester, respectively. For example a glycopeptide compound of formula I wherein R$^3$ is a nitrogen linked moiety comprising one or more phosphono groups can be prepared by coupling a corresponding glycopeptide compound of formula I wherein R$^3$ is hydroxy with the requisite phosphono-containing amine to form the formula I wherein R$^3$ is a nitrogen linked moiety comprising one or more phosphono groups.

A glycopeptide compound of the present invention, which is substituted at the C-terminus with a substituent that comprises one or more (e.g. 1, 2, 3, 4, or 5) phosphono (—PO$_3$H$_2$) groups, and wherein the vancosamine amino terminus (V) is substituted, can be prepared by first reductively alkylating the corresponding glycopeptide compound wherein the vancosamine amino terminus (V) is the free anine (NH$_2$) and then coupling the corresponding glycopeptide compound with the requisite phosphono containing compound (e.g. phosphono containing amine, alcohol, or thiol).

By way of illustration, a glycopeptide compound, such as vancomycin, can first be reductive alkylated as shown in the following reaction:

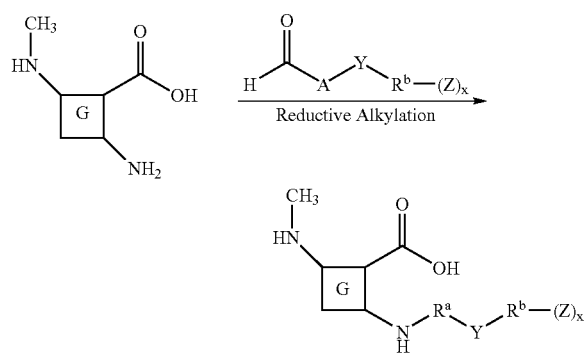

where A represents R$^a$ minus one carbon atom and R$^a$, R$^b$, Y, Z and x are as defined herein. This reaction is typically conducted by first contacting one equivalent of the glycopeptide, i.e., vancomycin, with an excess, preferably from 1.1 to 1.3 equivalents, of the desired aldehyde in the presence of an excess, preferably about 2.0 equivalents, of a tertiary amine, such as diisopropylethylamine (DIPEA) and the like. This reaction is typically conducted in an inert diluent, such as DMF or acetonitrile/water, at ambient temperature for about 0.25 to 2 hours until formation of the corresponding imine and/or hemiaminal is substantially complete. The resulting imine and/or hemiaminal is typically not isolated, but is reacted in situ with a reducing agent, such as sodium cyanoborohydride, pyridine borane, or the like, to afford the corresponding amine. This reaction is preferably conducted by contacting the imine and/or hemiaminal with an excess, preferably about 3 equivalents, of trifluoroacetic acid, followed by about 1 to 1.2 equivalents of the reducing agent at ambient temperature in methanol or acetonitrile/water. The resulting alkylated product is readily purified by conventional procedures, such as precipitation and/or reverse-phase HPLC. Surprisingly, by forming the imine and/or hemiaminal in the presence of a trialkyl amine, and then acidifying with trifluoroacetic acid before contact with the reducing agent, the selectivity for the reductive alkylating reaction is greatly improved, i.e., reductive alkylating at the amino group of the saccharide (e.g., vancosamine) is favored over reductive alkylating at the N-terminus (e.g., the leucinyl group) by at least 10:1, more preferably 20:1.

The above process is a significantly improvement over previous methods for selectively alkylating an amino saccharide group of a glycopeptide antibiotic. Thus, the present invention also provides a method for alkylating a glycopeptide that comprises a saccharide-amine comprising:

combining an aldehyde or ketone, a suitable base, and the glycopeptide, to provide a reaction mixture;

acidifying the reaction mixture; and combining the reaction mixture with a suitable reducing agent, to provide a glycopeptide that is alkylated at the saccharide-amine. Preferably, the glycopeptide comprises at least one amino group other than the saccharide-amine.

Preferably, the reductive alkylating at the saccharide-amine is favored over reductive alkylating at another amino group of the glycopeptide by at least about 10:1; and more preferably, by at least about 15:1 or about 20:1.

The reductive alkylating process of the invention is typically carried out in the presence of a suitable solvent or combination of solvents, such as, for example, a halogenated hydrocarbon (e.g. methylene chloride), a linear or branched ether (e.g. diethyl ether, tetrahydrofuran), an aromatic hydrocarbon (e.g. benzene or toluene), an alcohol (methanol, ethanol, or isopropanol), dimethylsulfoxide (DMSO), N,N-dimethylformamide, acetonitrile, water, 1,3-dimethyl-3,4,5,6-tetrahydro-2(1H)-pyrimidone, tetramethyl urea, N,N-dimethylacetamide, diethylformamide (DMF), 1-methyl-2-pyrrolidinone, tetramethylenesulfoxide, glycerol, ethyl acetate, isopropyl acetate, N,N-dimethylpropylene urea (DMPU) or dioxane. Preferably the alkylating is carried out in acetonitrile/water, or DMF/methanol.

Preferably the reduction (i.e. treatment with the reducing agent) is carried out in the presence of a protic solvent, such as, for example, an alcohol (e.g. methanol, ethanol, propanol, isopropanol, or butanol), water, or the like.

The reductive alkylating process of the invention can be carried out at any suitable temperature from the freezing point to the reflux temperature of the reaction mixture. Preferably the reaction is carried out at a temperature in the range of about 0° C. to about 100° C. More preferably at a temperature in a range of about 0° C. to about 50° C., or in a range of about 20° C. to about 30° C.

Any suitable base can be employed in the reductive alkylating process of the invention. Suitable bases include tertiary amines (e.g. diisopropylethylamine, N-methylmorpholine or triethylamine) and the like.

Any suitable acid can be used to acidify the reaction mixture. Suitable acids include carboxylic acids (e.g. acetic acid, trichloroacetic acid, citric acid, formic acid, or trifluoroacetic acid), mineral acids (e.g. hydrochloric acid, sulfuric acid, or phosphoric acid), and the like. A preferred acid is trifluoroacetic acid.

Suitable reducing agents for carrying out reductive alkylating process of the invention are known in the art. Any suitable reducing agent can be employed in the methods of the invention, provided it is compatible with the functionality present in the glycopeptide. For example, suitable reducing agents include sodium cyanoborohydride, sodium triacetoxyborohydride, pyridine/borane, sodium borohydride, and zinc borohydride. The reduction can also be carried out in the presence of a transition metal catalyst (e.g. palladium or platinum) in the presence of a hydrogen source (e.g. hydrogen gas or cyclohexadiene). See for example, *Advanced Organic Chemistry*, Fourth Edition, John Wiley & Sons, New York (1992), 899–900.

The glycopeptide derivative resulting from the reductive alkylating is then coupled with a phosphono containing amine ($R^3$—H) to form an amide bond. This reaction is illustrated by the following reaction:

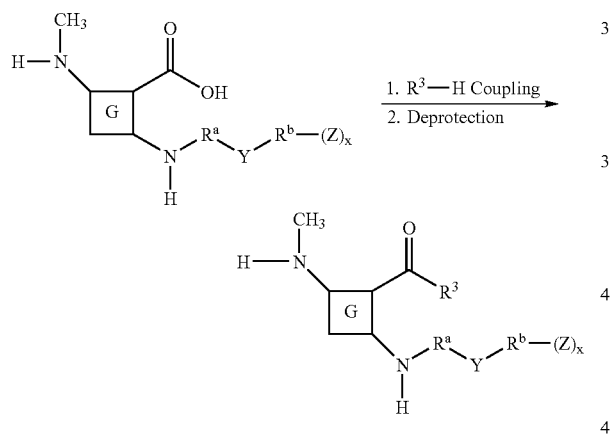

where $R^3$ is a nitrogen-linked group that comprises one or more phosphono groups. In this reaction, the glycopeptide derivative is typically contacted with the amine in the presence of a peptide coupling reagent, such as PyBOP and HOBT, to provide the amide. This reaction is typically conducted in an inert diluent, such as DMF, at a temperature ranging from about 0° C. to about 60° C. for about 1 to 24 hours or until the coupling reaction is substantially complete. Subsequent deprotection using conventional procedures and reagents affords the compound of this invention.

If desired, the amine coupling step described above can be conducted first to provide an amide, followed by reductive alkylating and deprotection to afford the compound of the invention.

If desired, the glycopeptide compounds of this invention can also be prepared in a step-wise manner in which a precursor to the —$R^a$—Y—$R^b$-$(Z)_x$ group is first attached the glycopeptide by reductive alkylation, followed by subsequent elaboration of the attached precursor using conventional reagent and procedures to form the —$R^a$Y—$R^b$-$(Z)_x$ group. Additionally, ketones may also be employed in the above-described reductive alkylating reactions to afford α-substituted amines.

Any glycopeptide having an amino group may be employed in these reductive alkylating reactions. Such glycopeptides are well-known in the art and are either commercially available or may be isolated using conventional procedures. Suitable glycopeptides are disclosed, by way of example, in U.S. Pat. Nos. 3,067,099; 3,338,786; 3,803,306; 3,928,571; 3,952,095; 4,029,769; 4,051,237; 4,064,233; 4,122,168; 4,239,751; 4,303,646; 4,322,343; 4,378,348; 4,497,802; 4,504,467; 4,542,018; 4,547,488; 4,548,925; 4,548,974; 4,552,701; 4,558,008; 4,639,433; 4,643,987; 4,661,470; 4,694,069; 4,698,327; 4,782,042; 4,914,187; 4,935,238; 4,946,941; 4,994,555; 4,996,148; 5,187,082; 5,192,742; 5,312,738; 5,451,570; 5,591,714; 5,721,208; 5,750,509; 5,840,684; and 5,843,889. Preferably, the glycopeptide employed in the above reaction is vancomycin.

As illustrated in the following scheme, a phosphono containing aminoalkyl sidechain at the resorcinol moiety of a glycopeptide, such as vancomycin, can be introduced via a Mannich reaction (in this scheme, the resorcinol moiety of the glycopeptide is illustrated for clarity). In this reaction, an amine of formula NHRR' (wherein one or both of R and R' is a group that comprises one or more phosphono groups), and an aldehyde (e.g. $CH_2O$), such as formalin (a source of formaldehyde), are reacted with the glycopeptide under basic conditions to give the glycopeptide derivative.

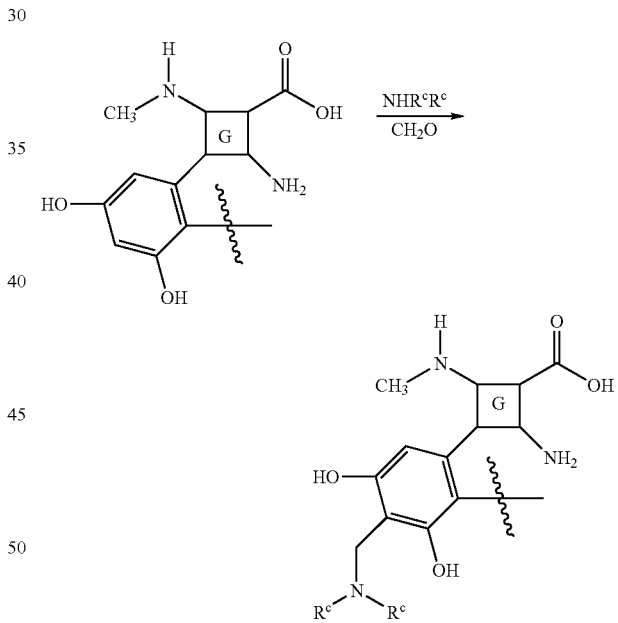

Compounds of the invention comprising a sulfoxide or sulfone can be prepared from the corresponding thio compounds using conventional reagents and procedures. Suitable reagents for oxidizing a thio compound to a sulfoxide include, by way of example, hydrogen peroxide, peracides such as 3-chloroperoxybenzoic acid (MCPBA), sodium periodate, sodium chlorite, sodium hypochlorite, calcium hypochlorite, tert-butyl hypochlorite and the like. Chiral oxidizing reagents, (optically active reagents) may also be employed to provide chiral sulfoxides. Such optically active reagents are well-known in the art and include, for example, the reagents described in Kagen et al., *Synlett.*, 1990,643–650.

The aldehydes and ketones employed in the above reactive alkylating reactions are also well-known in the art and are either commercially available or can be prepared by conventional procedures using commercially available starting materials and conventional reagents (for example see March, *Advanced Organic Chemistry,* Fourth Edition, John Wiley & Sons, New York (1992), and references cited therein).

The phosphono substituted compounds (e.g. the phosphono substituted amines, alcohols, or thiols) are either commercially available or can be prepared by conventional procedures using commercially available starting materials and reagents. See for example, *Advanced Organic Chemistry,* Jerry March, 4th ed, 1992, John Wiley and Sons, New York, page 959; and Frank R. Hartley (ed.) *The Chemistry of Organophosphorous Compounds,* vol. 1–4, John Wiley and Sons, New York (1996). Aminomethylphosphonic acid is commercially available from Aldrich Chemical Company, Milwaukee, Wis.

Additional details and other methods for preparing the compounds of this invention are described in the Examples below.

Pharmaceutical Compositions

This invention also includes pharmaceutical composition containing the novel glycopeptide compounds of this invention. Accordingly, the glycopeptide compound, preferably in the form of a pharmaceutically acceptable salt, can be formulated for oral or parenteral administration for the therapeutic or prophylactic treatment of bacterial infections.

By way of illustration, the glycopeptide compound can be admixed with conventional pharmaceutical carriers and excipients and used in the form of tablets, capsules, elixirs, suspensions, syrups, wafers, and the like. Such pharmaceutical compositions will contain from about 0.1 to about 90% by weight of the active compound, and more generally from about 10 to about 30%. The pharmaceutical compositions may contain common carriers and excipients, such as corn starch or gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

In a preferred embodiment, the glycopeptide derivatives of this invention are formulated in an aqueous solution containing a cyclodextrin. In another preferred embodiment the glycopeptide derivatives of this invention are formulated as a lyophilized powder containing a cyclodextrin or as a sterile powder containing a cyclodextrin. Preferably, the cyclodextrin is hydroxypropyl-β-cyclodextrin or sulfobutyl ether β-cyclodextrin; more preferably, the cyclodextrin is hydroxypropyl-β-cyclodextrin. Typically, in an injectable solution, the cyclodextrin will comprise about 1 to 25 weight percent; preferably, about 2 to 10 weight percent; more preferable, about 4 to 6 weight percent, of the formulation. Additionally, the weight ratio of the cyclodextrin to the glycopeptide derivative will preferably be from about 1:1 to about 10:1.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991. Such patches may be constructed for continuous, pulsatile, or on demand delivery of pharmaceutical agents.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses are in the general range of from 0.01–100 mg/kg/day, preferably 0.1–50 mg/kg/day. For an average 70 kg human, this would amount to 0.7 mg to 7 g per day, or preferably 7 mg to 3.5 g per day. A more preferred dose for a human is about 500 mg to about 2 g per day.

Other suitable formulations for use in the present invention can be found in *Remington's Pharmaceutical Sciences*, Mace Publishing Company, Philadelphia, Pa., 17th ed. (1985).

The following illustrate representative pharmaceutical compositions of the present invention.

Formulation Example A

This example illustrates the preparation of a representative pharmaceutical composition for oral administration of a compound of this invention:

| Ingredients | Quantity per tablet, (mg) |
| --- | --- |
| Active Compound | 200 |
| Lactose, spray-dried | 148 |
| Magnesium stearate | 2 |

The above ingredients are mixed and introduced into a hard-shell gelatin capsule.

Formulation Example B

This example illustrates the preparation of another representative pharmaceutical composition for oral administration of a compound of this invention:

| Ingredients | Quantity per tablet, (mg) |
| --- | --- |
| Active Compound | 400 |
| Cornstarch | 50 |
| Lactose | 145 |
| Magnesium stearate | 5 |

The above ingredients are mixed intimately and pressed into single scored tablets.

Formulation Example C

This example illustrates the preparation of a representative pharmaceutical composition for oral administration of a compound of this invention.

An oral suspension is prepared having the following composition.

| Ingredients | |
| --- | --- |
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Formulation Example D

This example illustrates the preparation of a representative pharmaceutical composition containing a compound of this invention.

An injectable preparation buffered to a pH of 4 is prepared having the following composition:

| Ingredients | |
| --- | --- |
| Active Compound | 0.2 g |
| Sodium Acetate Buffer Solution (0.4 M) | 2.0 ml |
| HCl (1N) | q.s. to pH 4 |
| Water (distilled, sterile) | q.s. to 20 ml |

Formulation Example E

This example illustrates the preparation of a representative pharmaceutical composition for injection of a compound of this invention.

A reconstituted solution is prepared by adding 20 ml of sterile water to 1 g of the compound of this invention. Before use, the solution is then diluted with 200 ml of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection Formulation Example F This example illustrates the preparation of a representative pharmaceutical composition containing a compound of this invention.

An injectable preparation is prepared having the following composition:

| Ingredients | |
|---|---|
| Active Compound | 0.1–5.0 g |
| Hydroxypropyl-β-cyclodextrin | 1–25 g |
| 5% Aqueous Dextrose Solution (sterile) | q.s. to 100 ml |

The above ingredients are blended and the pH is adjusted to 3.5±0.5 using 0.5 N HCl or 0.5 N NaOH.

Formulation Example G

This example illustrates the preparation of a representative pharmaceutical composition containing a compound of this invention.

A frozen solution suitable for injection is prepared having the following composition:

| Frozen Solution | |
|---|---|
| Active Compound | 250 mg to 1000 mg |
| Hydroxypropyl-β-cyclodextrin | 250 mg to 10 g |
| Excipients - e.g., dextrose | 0–50 g |
| Water for Injection | 10–100 ml |

The weight ratio of hydroxypropyl-β-cyclodextrin to the active compound will typically be from about 1:1 to about 10:1.

Representative Procedure: Hydroxypropyl-β-cyclodextrin and excipients, if any, are dissolved in about 80% of the water for injection and the active compound is added and dissolved. The pH is adjusted with 1 M sodium hydroxide to 4.7±0.3 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

Formulation Example H

This example illustrates the preparation of a representative pharmaceutical composition containing a compound of this invention.

A lyophilized powder useful for preparing an injectable solution is prepared having the following composition:

| Lyophilized Powder | |
|---|---|
| Active Compound | 250 mg to 1000 mg |
| Hydroxypropyl-β-cyclodextrin | 250 mg to 10 g |
| Excipients - e.g., mannitol, sucrose and/or lactose | 0–50 g |
| Buffer agent - e.g., citrate | 0–500 mg |

The weight ratio of hydroxypropyl-β-cyclodextrin to the active compound will typically be from about 1:1 to about 10:1.

Representative Procedure: Hydroxypropyl-β-cyclodextrin and excipients and/or buffering agents, if any, are dissolved in about 60% of the water for injection. The active compound is added and dissolved and the pH is adjusted with 1 M sodium hydroxide to 4.0–5.0 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored at room temperature or under refrigeration.

Formulation Example I

This example illustrates the preparation of a representative pharmaceutical composition containing a compound of this invention.

A sterile powder useful for preparing an injectable solution is prepared having the following composition:

| Sterile Powder | |
|---|---|
| Active Compound | 250 mg to 1000 mg |
| Hydroxypropyl-β-cyclodextrin | 250 mg to 10 g[1] |
| Excipients | optional |

The weight ratio of hydroxypropyl-β-cyclodextrin to the active will typically be from about 1:1 to about 10:1.

Representative Procedure: Hydroxypropyl-β-cyclodextrin and the active compound (and any excipients) are dispersed into an appropriate sterile container and the container is sealed (optionally under partial vacuum or dry nitrogen), labeled and stored at room temperature or under refrigeration.

Administration of Representative Formulations H and I to a Patient

The pharmaceutical formulations described in formulation examples H and I above can be administered intravenously to a patient by the appropriate medical personnel to treat or prevent gram-positive infections. For administration, the above formulations can be reconstituted and/or diluted with a diluent, such as 5% dextrose or sterile saline, as follows:

Representative Procedure: The lyophilized powder of formulation example H (e.g., containing 1000 mg of active compound) is reconstituted with 20 ml of sterile water and the resulting solution is further diluted with 80 ml of sterile saline in a 100 ml infusion bag. The diluted solution is then administered to the patient intravenously over 30 to 120 minutes.

Formulation Example J

This example illustrates the preparation of a representative pharmaceutical composition for topical application of a compound of this invention.

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Formulation Example K

This example illustrates the preparation of a representative pharmaceutical composition containing a compound of this invention.

A suppository totaling 2.5 grams is prepared having the following composition:

| Ingredients | |
|---|---|
| Active Compound | 500 mg |
| Witepsol H-15* | balance |

(*triglycerides of saturated vegetable fatty acid; a product of Riches-Nelson, Inc., New York, N.Y.)

A preferred active compound for incorporation in Formulations A–K is compound 11, or a pharmaceutically acceptable salt thereof (e.g. the hydrochloride salt).

Utility

The glycopeptide compounds of this invention, and their pharmaceutically acceptable salts, are useful in medical treatments and exhibit biological activity, including antibacterial activity, which can be demonstrated in using the tests described herein. Such tests are well known to those skilled in the art, and are referenced and described in Lorian "Antibiotics in Laboratory Medicine", Fourth Edition, Williams and Wilkins (1991).

Accordingly, this invention provides methods for treating bacterial or infectious diseases, especially those caused by Gram-positive microorganisms, in animals. The compounds of this invention are particularly useful in treating infections caused by methicillin-resistant staphylococci. Also, the compounds are useful in treating infection due to enterococci, including vancomycin-resistant enterococci (VRE). Examples of such diseases include severe staphylococcal infections, such as staphylococcal endocarditis and staphylococcal septicemia. The animal treated may be either susceptible to, or infected with, the microorganism. The method of treatment typically comprises administering to the animal an amount of a compound of this invention which is effective for this purpose.

In practicing this method, the antibiotic can be administered in a single daily dose or in multiple doses per day. The treatment regimen may require administration over extended periods of time, for example, for several days or for from one to six weeks. The amount per administered dose or the total amount administered will depend on such factors as the nature and severity of the infection, the age and general health of the patient, the tolerance of the patient to the antibiotic and the microorganism or microorganisms in the infection. Preferably, the compounds of the invention are administered intervenously.

Among other properties, the glycopeptide compounds of the invention have been found to have reduced mammalian toxicity when administered to a mammal. For example, the phosphono substituted derivatives of the invention have been found to have reduced liver and/or kidney accumulation compared to the corresponding non-phosphono substituted compounds. Moreover, certain compounds of this invention are expected to have reduced nephrotoxicity. Additionally, it has been discovered that the addition of a cyclodextrin compound to a pharmaceutical composition containing the glycopeptide compounds of this invention further reduces the nephrotoxicity and/or tissue accumulation of the glycopeptide compound when administered to a mammal.

The following synthetic and biological examples are offered to illustrate this invention and are not to be construed in any way as limiting the scope of this invention.

EXAMPLES

In the examples below, the following abbreviations have the following meanings. Any abbreviations not defined have their generally accepted meaning. Unless otherwise stated, all temperatures are in degrees Celsius.

ACN=acetonitrile
BOC, Boc=tert-butoxycarbonyl
DIBAL-H=diisobutylaluminum hydride
DIPEA=diisopropylethylamine
DMF=N,N-dimethylformamide
DMSO=dimethyl sulfoxide
eq.=equivalent
EtOAc=ethyl acetate
Fmoc=9-fluorenylmethoxycarbonyl
HOBT=1-hydroxybenzotriazole hydrate
Me=methyl
MS=mass spectroscopy
PyBOP=benzotriazol-1-yloxytris(pyrrolidino)phosphonium hexafluorophosphate
TEMPO=2,2,6,6-tetramethyl-piperidinyloxy, free radical
TFA=trifluoroacetic acid
THF=tetrahydrofuran
TLC, tlc=thin layer chromatography In the following examples, vancomycin hydrochloride semi-hydrate was purchased from Alpharma, Inc. Fort Lee, N.J. 07024 (Alpharma AS, Oslo Norway). Other reagents and reactants are available from Aldrich Chemical Co., Milwaukee, Wis. 53201.

General Procedure A

Reductive Alkylating of Vancomycin

To a mixture of vancomycin (1 eq.) and the desired aldehyde (1.3 eq.) in DMF was added DIPEA (2 eq.). The reaction was stirred at ambient temperature for 1–2 hours and monitored by reverse-phase HPLC. Methanol and NaCNBH$_3$ (1 eq.) were added to the solution, followed by TFA (3 eq.). Stirring was continued for an additional hour at ambient temperature. After the reaction was complete, the methanol was removed in vacuo. The residue was precipitated in acetonitrile. Filtration gave the crude product which was then purified by reverse-phase HPLC. If desired, other glycopeptides antibiotics may be used in this procedure.

General Procedure B

Synthesis of 2-(Decylthio)acetaldehyde

Under nitrogen, to a suspension of potassium carbonate (27 g, 200 mmol) in acetone (100 ml) was added decyl bromide (10 ml, 50 mmol) and mercaptoethanol (4.4 ml, 63 mmol). The suspension was stirred at room temperature for 2 days, then partitioned between water and 80% hexane/ethyl acetate. The organic phase was washed with 2N sodium hydroxide, dried over magnesium sulfate, and the volatiles removed under vacuum to give 2-(decylthio)ethanol (10.2 g, 47 mmol) as a colorless liquid that was used without further purification.

Under nitrogen, 2-(decylthio)ethanol (50 g, 230 mmol), N,N-diisopropylethylamine (128 ml, 730 mmol) and methylene chloride (400 ml) were cooled to −40° C. To this solution was added, over 15 minutes, a solution of sulfur trioxide pyridine complex (116 g, 730 mmol) in dimethyl sulfoxide (600 ml) and methylene chloride (200 ml). After addition, the mixture was stirred a further 15 minutes at −40° C., then 600 ml ice water as added. The mixture was removed from the cooling bath, 1 L water was added, and the liquids partitioned. The organic phase was washed with 1 L of 1 N hydrochloric acid, and dried over magnesium sulfate. Filtration gave 600 ml liquid, which was diluted with 600 ml hexane and passed through 200 ml silica. The silica was washed with 100 ml 50% methylene chloride/hexane, then 300 ml methylene chloride. The combined organics were concentrated in vacuo to give 2-decylthio)acetaldehyde (48 g, 220 mmol) as a colorless liquid that was used without further purification.

General Procedure C

Synthesis of $N^{van}$-2-(Decylthio)ethyl Vancomycin

Procedure A: Under nitrogen, vancomycin hydrochloride hydrate (1 g, 0.64 mmol) was added to 2-(decylthio)acetaldehyde (139 mg, 0.64 mmol) in N,N-dimethylformamide (8 ml). N,N-diisopropylethylamine (336 uL, 1.9 mmol) was added and the suspension stirred vigorously for 2.5 hours, over the course of which all the vancomycin dissolved. Solid sodium cyanoborohydride (60 mg, 0.96 mmol) was added, followed by methanol (5 ml) and trifluoroacetic acid (250 uL, 3.2 mmol). The reaction was stirred for 55 minutes at room temperature and analyzed by reverse phase HPLC. The product distribution based on uv absorption at 280 nm was as follows:

| Elution time (min) | Area % | Product |
|---|---|---|
| 2.0 | 29 | vancomycin |
| 3.1 | 50 | $N^{van}$-2-(decylthio)ethyl vancomycin |
| 3.2 | 2 | — |
| 3.3 | 7 | $N^{leu}$-2-(decylthio)ethyl vancomycin |
| 3.9 | 13 | $N^{van}$, $N^{leu}$-bis-[2-(decylthio)ethyl] vancomycin |
| 4.0 | 0.5 | — |

Procedure B: Under nitrogen, to a solution of 2-decylthio) acetaldehyde (crude, 48 g, 220 mmol) in N,N-dimethylformamide (1.4 L) was added solid vancomycin hydrochloride hydrate (173 g, 110 mmol) followed by N,N-diisopropylethylamine (58 ml, 330 mmol). The suspension was stirred vigorously at room temperature for 2 hours, in the course of which time all the vancomycin filly dissolved, then trifluoroacetic acid (53 ml, 690 mmol) was added. The solution was stirred a further 90 minutes, then solid sodium cyanoborohydride (10.5 g, 170 mmol) followed by methanol (800 ml) were added. After three hours the reaction was analyzed by reverse-phase HPLC. The product distribution based on uv absorption at 280 nm was as follows:

| Elution time (min) | Area % | Product |
|---|---|---|
| 2.0 | 15 | vancomycin |
| 3.2 | 77 | $N^{van}$-2-(decylthio)ethyl vancomycin |
| 3.3 | 3 | — |
| 3.4 | 0.5 | $N^{leu}$-2-(decylthio)ethyl vancomycin |
| 4.0 | 0.8 | $N^{van}$, $N^{leu}$-bis-[2-(decylthio)ethyl] vancomycin |
| 4.1 | 4 | — |

The reaction mixture from either of the above procedures was poured into water (7 L), resulting in a slightly cloudy solution. The pH of the solution was adjusted to 5 with saturated sodium bicarbonate, resulting in the formation of a white precipitate. This precipitate was collected by filtration, washed with water then ethyl acetate and dried under vacuum to afford $N^{van}$-2-(decylthio)ethyl vancomycin, which was used without further purification.

Procedure C: A solution of vancomycin hydrochloride (3.0 g, 2.1 mmol) in $ACN/H_2O$ (1:1, 30 ml) was treated with diisopropylethylamine (0.54 g, 0.72 ml, 4.2 mmol) followed by 2-(decylthio)acetaldehyde (0.91 g, 4.2 mmol) at 25° C. After 30 min, the reaction mixture was treated with TFA (1.92 g, 1.29 ml, 16.8 mmol) followed by $NaCNBH_3$ (0.132 g, 2.1 mmol). After 5 to 10 minutes, the crude product $N^{van}$-2-(decylthio)ethyl vancomycin is precipitated in acetonitrile (300 ml).

Example 1

Preparation of Compound 3 (Formula II wherein $R^3$ is N-(phosphonomethyl)amino; $R^5$ is hydrogen; $R^{19}$ is hydrogen, and $R^{20}$ is $-CH_2CH_2-S-(CH_2)_9CH_3$)

$N^{van}$-(2-decylthio)ethyl vancomycin bistrifluoroacetate (1 g, 0.53 mmol) and diisopropylethylamine (0.23 ml, 1.33 mmol) were combined in DMF (10 ml) and stirred until homogeneous. HOBt (0.080g, 0.58mmol) and PYBOP (0.300g, 0.58 mmol) were then added to the reaction mixture. After 5–10 minutes a homogeneous solution containing (aminomethyl)phosphonic acid (0.060 g, 0.53 mmol) and diisopropylethylamine (0.23 ml, 1.33 mmol) in water (3 ml) was added. The reaction was stirred at room temperature and monitored by MS. When the reaction was judged to be complete, the reaction mixture was diluted with acetonitrile (40 ml) and centrifuged. The supernatant was discarded and the remaining pellet containing desired product was dissolved in 50% aqueous acetonitrile (10 ml) and purified by reverse phase preparative HPLC to give the title compound. MS calculated (M+) 1742.7; found (MH+) 1743.6.

Example 2

Preparation of Compound 11 (Formula II wherein $R^3$ is —OH; $R^5$ N-(phosphonomethyl)-aminomethyl; $R^{19}$ is hydrogen, and $R^{20}$ is $-CH_2CH_2-NH-(CH_2)_9CH_3$)

(Aminomethyl)phosphonic acid (3.88 g, 35 mmol) and diisopropylethylamine (6.1 ml, 35 mmol) were combined in water (40 ml) and stirred until homogeneous. Acetonitrile (50 ml) and formaldehyde (37% solution in $H_2O$; 0.42 ml, 05.6 mmol) were then added to the reaction mixture. After approximately 15 minutes both $N^{van}$-decylaminoethyl vancomycin tristrifluoroacetate (10.0 g, 5.1 mmol) and diisopropylethylamine (6.1 ml, 35 mmol) were added to the reaction mixture. The reaction was stirred at room temperature for approximately 18 hrs, at which time the pH was adjusted to about 7 with 20% TFA, acetonitrile was removed in vacuo, and the residue was lyophilized. The resulting solid was triturated with water (100 mL), collected by filtration, dried in vacuo and purified by reverse phase preparative HPLC to give the title compound. MS calculated (MH+) 1756.6; found (MH+) 1756.6.

Compound 11 was also prepared as follows.

The quinuclidine salt of $N^{van}$-(decylaminoethyl)vancomycin (500 mg, 0.28 mmol, sub-part f below) and aminomethylphosphonic acid (155 mg, 1.4 mmol) were slurried in 50% aqueous acetonitrile (10 mL). Diisopropyl-ethylamine (972 uL, 720 mg, 5.6 mmol) was added and the mixture stirred at room temperature until the solids had dissolved. The reaction mixture was then cooled in an ice bath and formalin (3.7%, made by diluting commercial 37% formalin 1:9 with 50% ACN/water, 220 uL, 8.8 mg, 0.29 mmol) was added. The reaction mixture was stirred at 0° for 15 hours, at which time the reaction to be complete. The reaction was quenched at 0° by adding 3N HCl to about pH 2. The mixture was diluted to 50 mL with 50% ACN/water, and then acetonitrile was added (75 mL, followed by 5×10 mL at 5 minute intervals, 125 mL total) to precipitate the product. The solid was collected by vacuum filtration and dried in vacuo. Purification by reverse phase preparative HPLC gave the title compound.

The intermediate $N^{van}$-decylaminoethyl vancomycin tris-trifluoroacetate was prepared as follows.

a. N-Fmoc-2-(decylamino)ethanol. 2-(n-Decylamino)ethanol (2.3 g, 11 mmol, 1.1 eq) and DIPEA (2.0 ml, 11 mmol, 1.1 eq) were dissolved in methylene chloride (15 ml) and cooled in an ice bath. 9-Fluorenylmethyl chloroformate (2.6 g, 10 mmol, 1.0 eq) in methylene chloride (15 ml) was added, the mixture stirred for 30 minutes then washed with 3N hydrochloric acid (50 ml) twice and saturated sodium bicarbonate (50 ml). The organics were dried over magnesium sulfate, and the solvents removed under reduced pressure. N-Fmoc-2-(decylamino)ethanol (4.6 g, 11 mmol, 108%) was used without further purification.

b. N-Fmoc-decylaminoacetaldehyde. To a solution of oxalyl chloride (12.24 ml) and methylene chloride (50 mL) at −35 to −45° C. was added DMSO (14.75 g) in methylene chloride (25 mL) over 20 minutes. The reaction mixture was stirred for 10 minutes at −35 to −45° C. A solution of N-Fmoc-decylaminoethanol (20.0 g) in methylene chloride (70 mL) was added over 25 minutes and then stirred 40 minutes at −35 to −45° C. Triethylamine (21.49 g) was then added and the mixture stirred for 30 minutes at −10 to −20° C. The reaction mixture was quenched with water (120 mL) followed by concentrated sulfuric acid (20.0 g) while maintaining the internal temperature at 0–5° C. The organic layer was isolated and washed with 2% sulfuric acid (100 mL) followed by water (2×100 mL). The organic solution was distilled under vacuum at 60° C. to about 100 mL. Heptane (100 mL) was added, the temperature of the oil bath raised to 80° C. and the distillation was continued until the residual volume was 100 mL. More heptane (100 mL) was added and the distillation repeated to a volume of 100 mL. The heating bath was replaced with a cold water bath at 15° C. The bath was cooled slowly to 5° C. over 20 minutes to start the precipitation of the product. The slurry was then cooled to −5 to −10° C. and the slurry was stirred for 2 hours. The solid was then collected on a Buchner funnel and washed with cold (−5° C.) heptane (2×15 mL). The wet solid was dried in vacuo to yield the aldehyde.

c. $N^{van}$-N-Fmoc-2-n-decylaminoethyl) vancomycin trifluoroacetate. Vancomycin hydrochloride (12 g, 7.7 mmol, 1.0 eq), N-Fmoc-2-(n-decylamino)acetaldehyde (3.2 g, 7.6 mmol, 1.0 eq) and DIPEA (2.6 ml, 14.9 mmol, 2.0 eq) were stirred at room temperature in DMF (120 ml) for 90 minutes. Sodium cyanoborohydride (1.4 g, 22 mmol, 3.0 eq) was added, followed by methanol (120 ml) then trifluoroacetic acid (1.8 ml, 23 mmol, 3.0 eq). The mixture was stirred for 60 minutes at room temperature, then the methanol removed under reduced pressure. The resulting solution was added to 600 ml diethyl ether giving a precipitate which was filtered, washed with ether, and dried under vacuum. The crude product was purified on a reverse-phase flash column, eluting with 10, 20, 30% acetonitrile in water (containing 0.1% trifluoroacetic acid) to remove polar impurities (such as residual vancomycin) then the product was eluted with 70% acetonitrile in water (containing 0.1 % trifluoroacetic acid) to give 9 g of $N^{van}$-(N-Fmoc-2-n-decylaminoethyl) vancomycin as its trifluoroacetate salt (4.3 mmol, 56%).

d. $N^{van}$-2-(n-Decylamino)ethyl vancomycin trifluoroacetate. $N^{van}$-(N-Fmoc-2-n-decylaminoethyl) vancomycin (100 mg) was dissolved in 1 ml DMF (1 ml) and treated with piperidine (200 uL) for 30 minutes. The mixture was precipitated into ether, centrifuged and washed with acetonitrile. Reverse-phase preparative HPLC (10–70% acetonitrile in water containing 0.1% trifluoroacetic acid over 120 minutes) gave $N^{van}$-2-(n-decylamino)ethyl vancomycin as its TFA salt.

The intermediate quinuclidine salt of $N^{van}$-decylaminoethyl vancomycin was prepared as follows.

e. $N^{van}$-(N'-Fmoc-decylaminoethyl) vancomycin. To a 2 L flask equipped with a mechanical stirrer was added vancomycin hydrochloride (50.0 g), N-Fmoc-decylaminoacetaldehyde (13.5 g), DMF (400 mL) and N,N-diisopropylethylamine (11.7 mL). The suspension was stirred at room temperature for 2 hours, at which time the solids had dissolved. Methanol (190 mL) followed by trifluoroacetic acid (10.4 mL) was added. After the reaction mixture had stirred for 5 minutes, borane-pyridine complex (3.33 g) was added in one portion, and rinsed in with methanol (10 mL). After stirring 4 hours, the reaction was cooled to 5–10° C. with an ice bath and water (675 mL) was added at a rate to keep the temperature below 20° C. The reaction mixture was warmed to room temperature and 10% NaOH was added to pH 4.2–4.3 (approx 15 mL). The resultant slurry was cooled in an ice bath for 1 hour, and then the product is collected by vacuum filtration and washed with cold water (2×100 mL). The wet solid was dried in vacuo at 50° C. to give the title compound as an off-white to pale-pink solid.

f. $N^{van}$-(decylaminoethyl) vancomycin quinuclidine salt. $N^{van}$-(N'-Fmoc-decylaminoethyl) vancomycin (88 g, 42 mmol) was dissolved in DMF (500 mL) by stirring at room temperature for 1 hour. Quinuclidine ( 9.4 g, 84 mmol) was added, and the reaction mixture stirred for 18 hours. The DMF was removed in vacuo and the solid was triturated with acetonitrile (700 mL) for 3 hours. The solid was collected on a Buchner funnel and triturated with acetonitrile (200 mL) for 16 hours. More acetonitrile (700 mL) was added at this time, and the solid was collected on a Buchner funnel, washed with acetonitrile (500 mL), and then resuspended in acetonitrile (500 mL). After stirring for 2 hours, the solid was collected on a Buchner funnel and dried in vacuo to give the title compound.

Example 3

Preparation of Compound 12 (Formula II wherein $R^3$ is —OH; $R^5$N-phosphonomethyl)aminomethyl; $R^{19}$ is hydrogen, and $R^{20}$ is —CH$_2$CH$_2$—S—(CH$_2$)$_9$CH$_3$)

(Aminomethyl)phosphonic acid (0.295 g, 266 mmol) and diisopropylethylamine (0.649 ml, 3.72 mmol) were combined in water (5 ml) and stirred until homogeneous. Formaldehyde (37% solution in H$_2$O; 0.044 ml, 0.585 mmol) and acetonitrile (5 ml) were then added to the reaction mixture. After approximately 15 minutes both $N^{van}$-(2-decylthio) ethyl vancomycin bistrifluoroacetate (1 g, 0.53 mmol) and diisopropylethylamine (0.649 ml, 3.72 mmol) were added to the reaction mixture. The reaction was stirred at room temperature for approximately 18 hrs, at which time the reaction mixture was diluted with ACN (40 ml) and centrifuged. The supernatant was discarded and the remaining pellet containing desired product was dissolved in 50% aqueous acetonitrile (10 ml) and purified by reverse phase preparative HPLC to give the title compound. MS calculated (M+) 1772.7; found (MH+) 1773.4.

Using the above procedures and the appropriate starting materials the compounds shown in Table I were prepared. The mass spectral data for these compounds were as follows:

| Compound No. | MW (freebase) | Observed MH+ |
|---|---|---|
| 1 | 1725.63 | 1726.6 |
| 2 | 1726.62 | 1727.5 |
| 3 | 1742.68 | 1743.6 |
| 4 | 1724.64 | 1725.6 |
| 5 | 1742.96 | 1743.6 |
| 6 | 1786.03 | 1786.4 |
| 7 | 1785.04 | 1785.8 |
| 8 | 1799.07 | 1799.7 |
| 9 | 1770.74 | 1771.8 |
| 10 | 1772.99 | 1774.3 |
| 11 | 1755.66 | 1756.6 |
| 12 | 1772.71 | 1773.4 |
| 13 | 1756.64 | 1757.6 |
| 14 | 1754.67 | 1755.7 |
| 15 | 1772.99 | 1773.7 |
| 16 | 1816.06 | 1816.5 |
| 17 | 1815.01 | 1816.2 |
| 18 | 1829.10 | 1829.8 |
| 19 | 1878.1 | 1878.2 |
| 20 | 1802.74 | 1803.5 |
| 21 | 1830.75 | 1831.7 |
| 22 | 1849.66 | 1850.6 |
| 23 | 1800.76 | 1801.6 |
| 24 | 1801.04 | 1801.6 |
| 25 | 1932.86 | 1934.0 |
| 26 | 1880.12 | 1880.7 |

Example 4

Preparation of an Intermediate Useful for Preparing a Compound of the Invention (Formula II wherein $R^3$ is —OH; $R^5$ is H; $R^{19}$ is Hydrogen, and $R^{20}$ is 4-(4-chlorophenyl)benzyl A three liter 3-necked flask was fitted with a condenser, nitrogen inlet and overhead mechanical stirring apparatus. The flask was charged with pulverized A82846B acetate salt (20.0 g, $1.21 \times 10^{-5}$ mol) and methanol (1000 ml) under a nitrogen atmosphere, 4'-chlorobiphenylcarboxaldehyde (2.88 g, $1.33 \times 10^{-2}$ mol, 1.1 eq.) was added to this stirred mixture, followed by methanol (500 ml). Finally, sodium cyanoborohydride (0.84 g, $1.33 \times 10^{-2}$ mol, 1.1 eq.) was added followed by methanol (500 ml). The resulting mixture was heated to reflux (about 65° C.).

After 1 hour at reflux, the reaction mixture attained homogeneity. After 25 hours at reflux, the heat source was removed and the clear reaction mixture was measured with a pH meter (6.97 at 58.0° C.). 1N NaOH (22.8 ml) was added dropwise to adjust the pH to 9.0 (at 54.7° C.). The flask was equipped with a distillation head and the mixture was concentrated under partial vacuum to a weight of 322.3 grams while maintaining the pot temperature between 40°–45° C.

The distillation head was replaced with an addition funnel containing 500 ml of isopropanol (IPA). The IPA was added dropwise to the room temperature solution over 1 hour. After approximately ⅓ of the IPA was added, a granular precipitate formed. The remaining IPA was added at a faster rate after precipitation had commenced. The flask was weighed and found to hold 714.4 grams of the IPA/methanol slurry.

The flask was reequipped with a still-head and distilled under partial vacuum to remove the remaining methanol. The resulting slurry (377.8 g) was allowed to chill in the freezer overnight. The crude product was filtered through a polypropylene pad and rinsed twice with 25 ml of cold IPA. After pulling dry on the funnel for 5 minutes, the material was placed in the vacuum oven to dry ta 40° C. A light pink solid (22.87 g (theory=22.43 g)) was recovered. HPLC analysis versus a standard indicated 68.0% weight percent of the title compound (4-[4-chlorophenyl]benzyl-A82846B] in the crude solid, which translated into a corrected crude yield of 69.3%.

The products of the reaction were analyzed by reverse-phase HPLC utilizing a Zorbax SB-$C_{18}$ column with ultraviolet light (UV; 230 nm) detection. A 20 minute gradient solvent system consisting of 95% aqueous buffer/5% $CH_3CN$ at time=0 minutes to 40% aqueous buffer/60% $CH_3CN$ at time=30 minutes was used, where the aqueous buffer was TEAP (5 ml $CH_3CN$, 3 ml phosphoric acid in 1000 ml water).

The intermediate A82846B acetate salt can be prepared as described in U.S. Pat. No. 5,840,684.

Using procedures described hereinabove, the product of Example 4 can be converted to a compound of the invention wherein $R^3$ and/or $R^5$ is a substituent that comprises one or more phosphono groups.

Example 5

Determination of Antibacterial Activity

A. In Vitro Determination of Antibacterial Activity

1. Determination of Minimal Inhibitory Concentrations (MICs)

Bacterial strains were obtained from either American Type Tissue Culture Collection (ATCC), Stanford University Hospital (SU), Kaiser Permanente Regional Laboratory in Berkeley (KPB), Massachusetts General Hospital (MGH), the Centers for Disease Control (CDC), the San Francisco Veterans' Administration Hospital (SFVA) or the University of California San Francisco Hospital (UCSF). Vancomycin resistant enterococci were phenotyped as Van A or Van B based on their sensitivity to teicoplanin. Some vancomycin resistant enterococci that had been genotyped as Van A, Van B, Van C1 or Van C2 were obtained from the Mayo Clinic.

Minimal inhibitory concentrations (MICs) were measured in a microdilution broth procedure under NCCLS guidelines. Routinely, the compounds were serially diluted into Mueller-Hinton broth in 96-well microtiter plates. Overnight cultures of bacterial strains were diluted based on absorbance at 600 nm so that the final concentration in each well was $5 \times 10^5$ cfu/ml. Plates were returned to a 35° C. incubator. The following day (or 24 hours in the case of *Enterococci* strains), MICs were determined by visual inspection of the plates. Strains routinely tested in the initial screen included methicillin-sensitive *Staphylococcus aureus* (MSSA), methicillin-resistant *Staphylococcus aureus*, methicillin-sensitive *Staphylococcus epidermidis* (MSSE), methicillin-resistant *Staphylococcus epidermidis* (MSSE), vancomycin sensitive *Enterococcus faecium* (VSE Fm), vancomycin sensitive *Enterococcus faecalis* (VSE Fs), vancomycin resistant *Enterococcus faecium* also resistant to teicoplanin (VRE Fm Van A), vancomycin resistant *Enterococcus faecium* sensitive to teicoplanin (VRE Fm Van B), vancomycin resistant *Enterococcus faecalis* also resistant to teicoplanin (VRE Fs Van A), vancomycin resistant *Enterococcus*

*faecalis* sensitive to teicoplanin (VRE Fs Van B), *enterococcus gallinarium* of the Van A genotype (VRE Gm Van A), *enterococcus gallinarium* of the Van C-1 genotype (VRE Gm Van C-1), *enterococcus casseliflavus* of the Van C-2 genotype (VRE Cs Van C-2), *enterococcus flavescens* of the Van C-2 genotype (VRE Fv Van C-2), and penicillin-sensitive *Streptococcus pneumoniae* (PSSP) and penicillin-resistant *Streptococcus pneumoniae* (PSRP). Because of the inability of PSSP and PSRP to grow well in Mueller-Hinton broth, MICs with those strains were determined using either TSA broth supplemented with defibrinated blood or blood agar plates. Compounds which had significant activity against the strains mentioned above were then tested for MIC values in a larger panel of clinical isolates including the species listed above as well as non-speciated coagulase negative *Staphylococcus* both sensitive and resistant to methicillin (MS-CNS and MR-CNS). In addition, they were tested for MICs against gram negative organisms, such as *Escherichia coli* and *Pseudomonas aeruginosa*.

2. Determination of Kill Time

Experiments to determine the time required to kill the bacteria were conducted as described in Lorian, "Antibiotics in Laboratory Medicine", Fourth Edition, Williams and Wilkins (1991). These experiments were conducted normally with both *staphylococcus* and *enterococcus* strains.

Briefly, several colonies were selected from an agar plate and grown at 35° C. under constant agitation until it achieved a turbidity of approximately 1.5 and $10^8$ CFU/ml. The sample was then diluted to about $6\times10^6$ CFU/ml and incubated at 35° C. under constant agitation was continued. At various times aliquots were removed and five ten-fold serial dilutions were performed. The pour plate method was used to determine the number of colony forming units (CFUs).

In general, the compounds of the invention were active in the above tests in vitro tests and demonstrated a broad spectrum of activity.

B. In Vivo Determination of Antibacterial Activity

1. Acute Tolerability Studies in Mice

In these studies, a compound of this invention was administered either intravenously or subcutaneously and observed for 5–15 minutes. If there were no adverse effects, the dose was increased in a second group of mice. This dose incrementation continued until mortality occurred, or the dose was maximized. Generally, dosing began at 20 mg/kg and increased by 20 mg/kg each time until the maximum tolerated dose (MTD) is achieved.

2. Bioavailability Studies in Mice

Mice were administered a compound of this invention either intravenously or subcutaneously at a therapeutic dose (in general, approximately 50 mg/kg). Groups of animals were placed in metabolic cages so that urine and feces could be collected for analysis. Groups of animals (n=3) were sacrificed at various times (10 min, 1 hour and 4 hours). Blood was collected by cardiac puncture and the following organs were harvested—lung, liver, heart, brain, kidney, and spleen. Tissues were weighed and prepared for HPLC analysis. HPLC analysis on the tissue homogenates and fluids was used to determine the concentration of the test compound or IiI present. Metabolic products resulting from changes to the test compound were also determined at this juncture.

3. Mouse Septicemia Model

In this model, an appropriately virulent strain of bacteria (most commonly *S. aureus*, or *E. Faecalis* or *E. Faecium*) was administered to mice (N=5 to 10 mice per group) intraperitoneally. The bacteria was combined with hog gastric mucin to enhance virulence. The dose of bacteria (normally $10^5$–$10^7$) was that sufficient to induce mortality in all of the mice over a three day period. One hour after the bacteria was administered, a compound of this invention was administered in a single dose either IV or subcutaneously. Each dose was administered to groups of 5 to 10 mice, at doses that typically ranged from a maximum of about 20 mg/kg to a minimum of less than 1 mg/kg. A positive control (normally vancomycin with vancomycin sensitive strains) was administered in each experiment. The dose at which approximately 50% of the animals are saved was calculated from the results.

4. Neutropenic Thigh Model

In this model, antibacterial activity of a compound of this invention was evaluated against an appropriately virulent strain of bacteria (most commonly *S. aureus*, or *E. Faecalis* or *E. Faecium*, sensitive or resistant to vancomycin). Mice were initially rendered neutropenic by administration of cyclophosphamide at 200 mg/kg on day 0 and day 2. On day 4 they were infected in the left anterior thigh by an IM injection of a single dose of bacteria. The mice were then administered the test compound one hour after the bacteria and at various later times (normally 1, 2.5, 4 and 24 hours) the mice were sacrificed (3 per time point) and the thigh excised, homogenized and the number of CFUs (colony forming units) were determined by plating. Blood was also plated to determine the CFUs in the blood.

5. Pharmacokinetic Studies

The rate at which a compound of this invention is removed from the blood can be determined in either rats or mice. In rats, the test animals were cannulated in the jugular vein. The test compound was administered via tail vein injection, and at various time points (normally 5, 15, 30, 60 minutes and 2,4,6 and 24 hours) blood was withdrawn from the cannula In mice, the test compound was also administered via tail vein injection, and at various time points. Blood was normally obtained by cardiac puncture. The concentration of the remaining test compound was determined by HPLC.

In general, the compounds of the invention were active in the above test in vivo and demonstrated a broad spectrum of activity.

Example 6

Determination of Tissue Accumulation

A. Tissue Distribution Using Radiolabeled Compound

This procedure is used to examine the tissue distribution, excretion and metabolism of a radiolabeled test compound in both male and female rats following intravenous infusion at 10 mg/kg. Male and female Sprague-Dawley rats (n =2 per sex per compound) are dosed with $^3$H-labeled test compound at 10 (400 µCi/kg) and 12.5 mg/kg (100 µCi/kg), respectively, via intravenous infusion (~2 min). The test compound is formulated in 5% hydroxypropyl-β-cyclodextrin as 2.5 mg/ml solution. Urine and feces are cage collected over 24 hours period. At 24 hours after dosing, animals are sacrificed and tissues are removed. Serum, urine and tissues are analyzed for total radioactivity by oxidation followed by liquid scintillation counting. Urine and selected tissues samples are extracted and analyzed by reverse phase HPLC with radioactive flow detector for the presence of potential metabolites.

B. Tissue Accumulation Following Single Dose

This procedure is used to evaluate tissue distribution of a test compound in rats following single dose administration by infusion. Male Sprague-Dawley rats (n=3 per dose groups) are dosed with 50 mg/kg of a test compound. Two formulations are used: 30% PEG 400 and 10% sulfobutylether-β-cyclodextrin. Urine samples are cage collected over 24 hours. Blood samples are collected for serum chemistry and concentration determination. Liver and kidneys are removed for histology evaluation. One kidney and part of the liver are homogenized for concentration analysis using reverse phase HPLC with UV detection. Drug concentrations in urine and serum samples are determined by LC-MS analysis.

C. Tissue Distribution Following Multiple Doses

This procedure is used to evaluate the potential tissue accumulation of a test compound in rats following multiple dose administration by intravenous infusion. Male and female Sprague-Dawley rats (n=4 per sex per dose group) are dosed with a test compound at 12.5, 25 and 50 mg/kg per day for seven days. Animals are sacrificed at day 1 (n=3 per sex per dose group) following the last dose administered. One animal per sex per dose group is retained as recovery animal and sacrificed at day 7 following the last dose administered. The test compound is formulated in 5% hydroxypropyl-β-cyclodextrin or 1% sucrose/4.5% dextrose. Urine samples are cage collected at days 1 and 7 post-dose. Blood samples are collected for serum chemistry and concentration determination. Liver and kidneys are removed for histology evaluation. One kidney and part of the liver are homogenized for concentration analysis using reverse phase HPLC with UV detection. Drug concentrations in urine and serum samples are determined by LC-MS analysis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Additionally, all publications, patents, and patent documents cited hereinabove are incorporated by reference herein in full, as though individually incorporated by reference.

What is claimed is:

1. A compound of the formula:

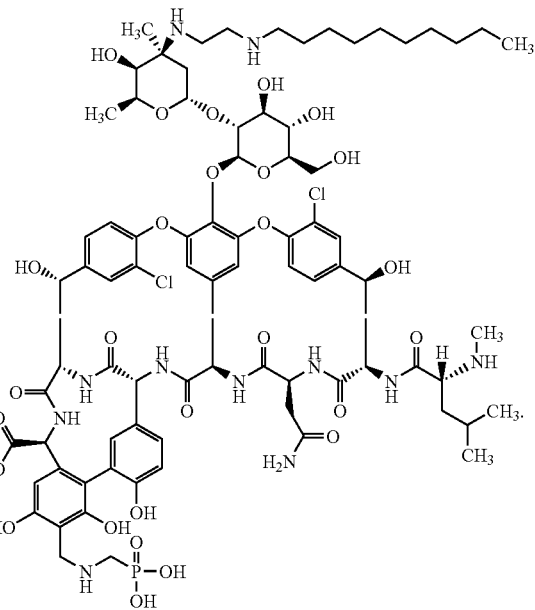

2. A pharmaceutically acceptable salt of a compound of the formula:

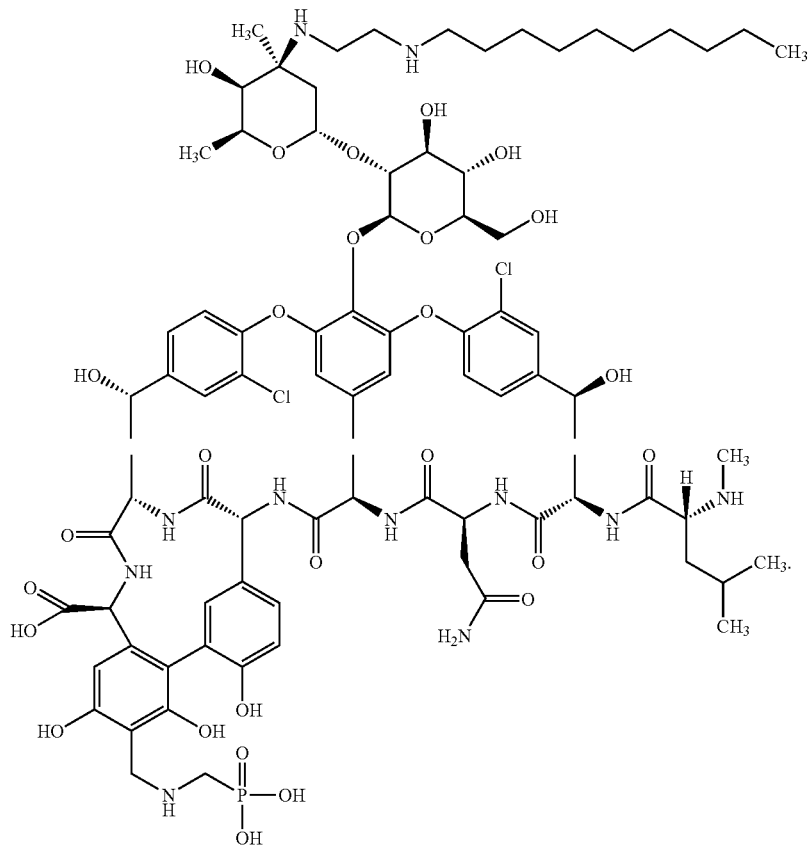

3. A pharmaceutical composition comprising a pharmaceutically acceptable carrier and a therapeutically effective amount of a compound of the formula:
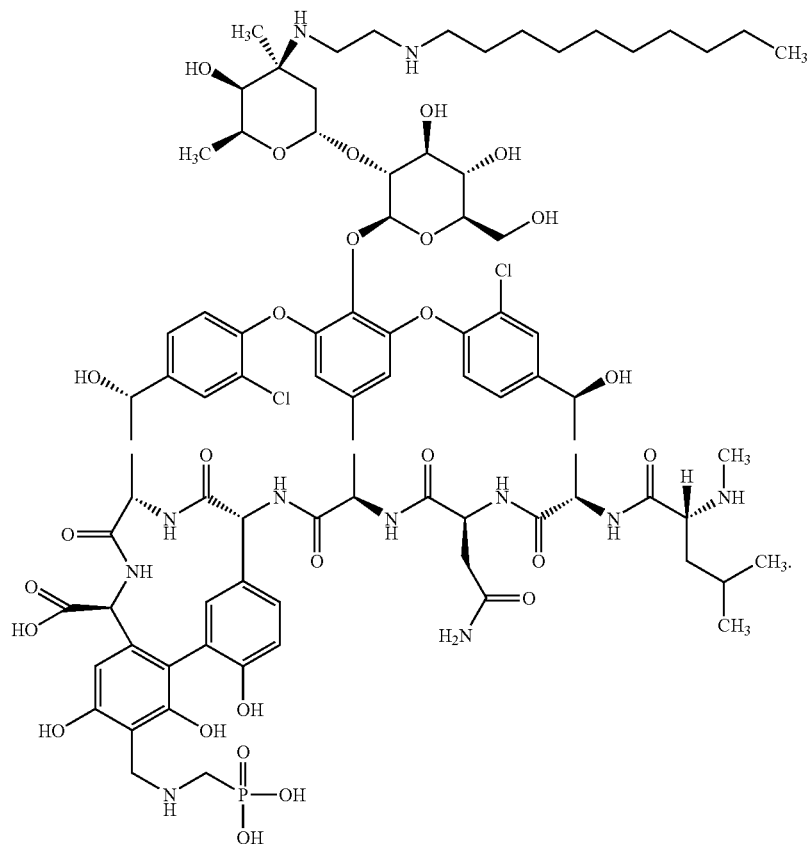
4. A pharmaceutical composition comprising a pharmaceutically acceptable carrier and a therapeutically effective amount of a pharmaceutically acceptable salt of a compound of the formula:
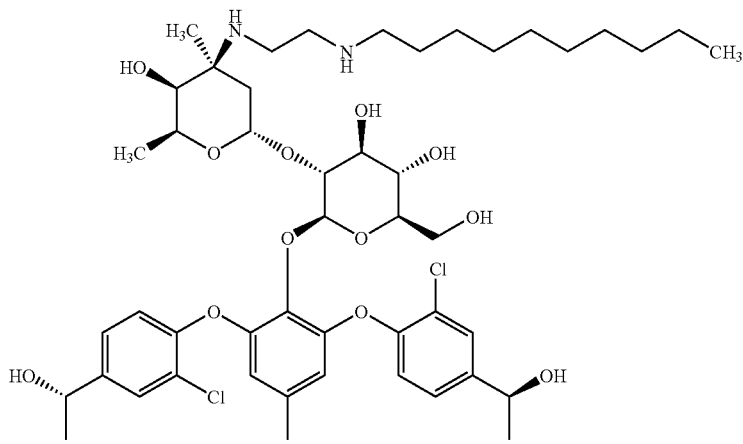

-continued
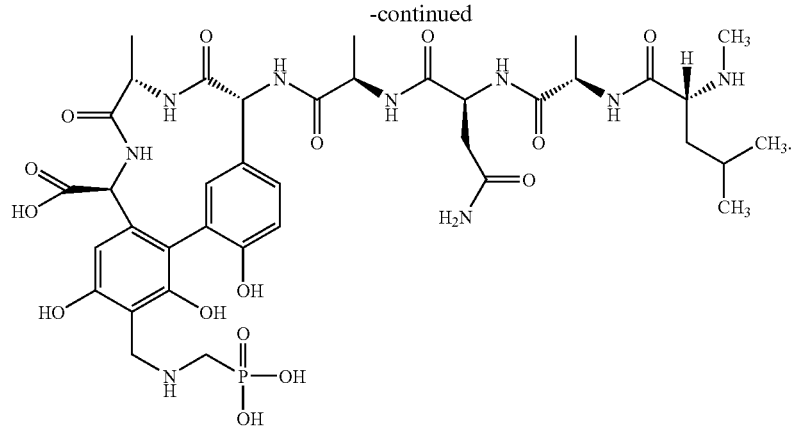
5. A pharmaceutical composition comprising a pharmaceutically acceptable carrier and a therapeutically effective amount of a hydrochloride salt of a compound of the formula:
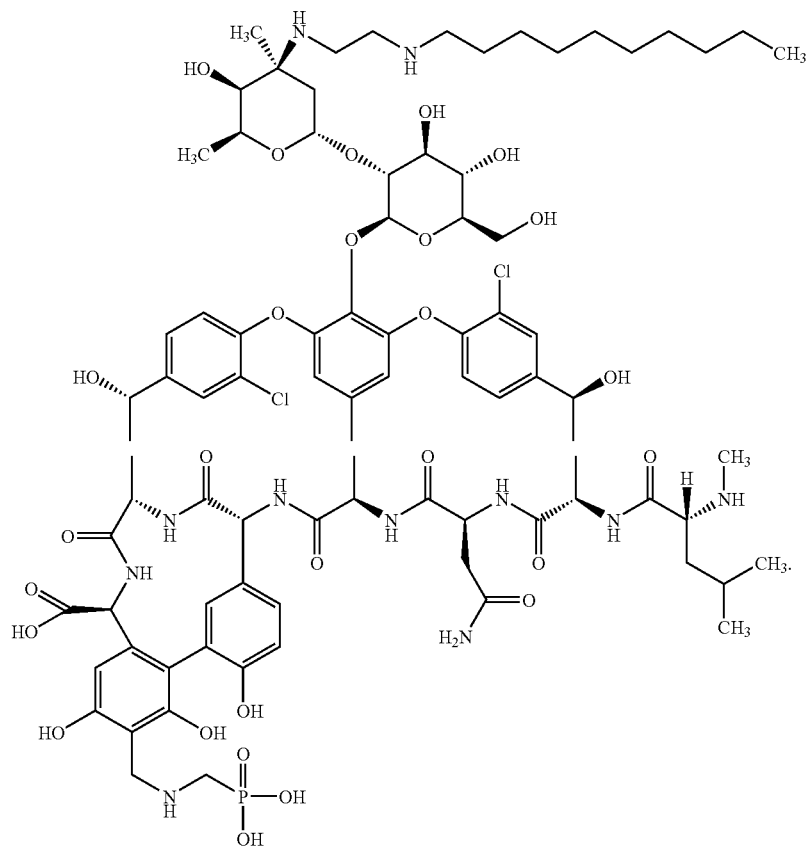

UNITED STATES PATENT AND TRADEMARK OFFICE
CERTIFICATE OF CORRECTION

| | | |
|---|---|---|
| PATENT NO. | : 7,208,471 B2 | Page 1 of 5 |
| APPLICATION NO. | : 11/265570 | |
| DATED | : April 24, 2007 | |
| INVENTOR(S) | : Michael R. Leadbetter | |

It is certified that error appears in the above-identified patent and that said Letters Patent is hereby corrected as shown below:

<u>Column 48</u>
at lines 8-30, in Claim 1, replace the structure after "a compound of the formula:" with the following structure:

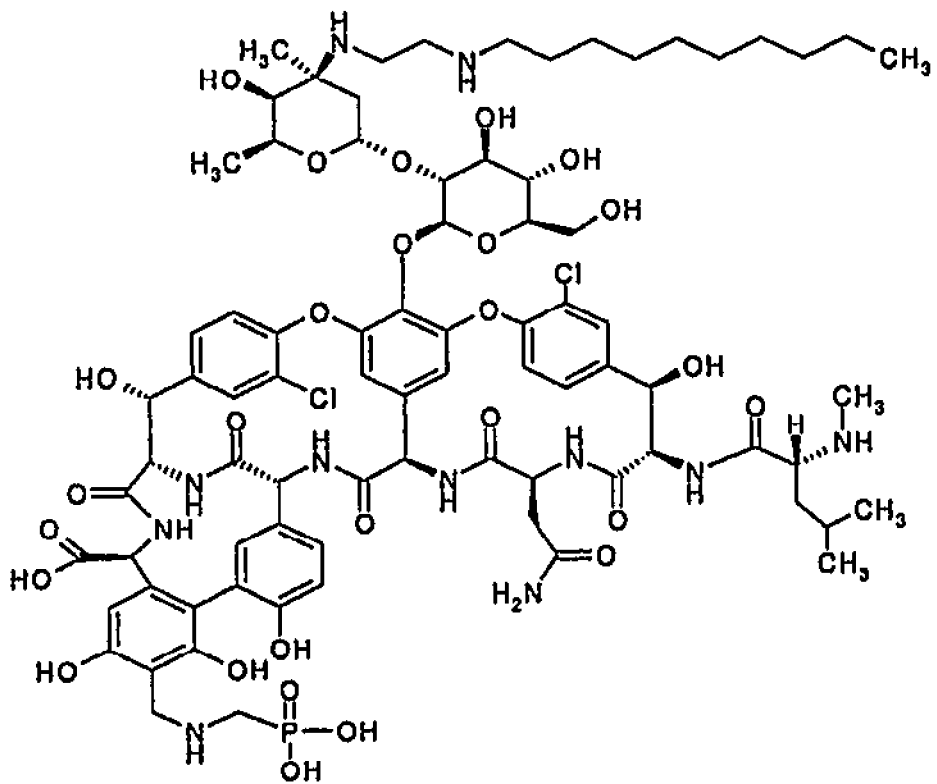

UNITED STATES PATENT AND TRADEMARK OFFICE
CERTIFICATE OF CORRECTION

PATENT NO.         : 7,208,471 B2                           Page 2 of 5
APPLICATION NO. : 11/265570
DATED              : April 24, 2007
INVENTOR(S)        : Michael R. Leadbetter It is certified that error appears in the above-identified patent and that said Letters Patent is hereby corrected as shown below:

Column 48
at lines 35-65, in Claim 2, replace the structure after "a compound of the formula:" with the following structure:

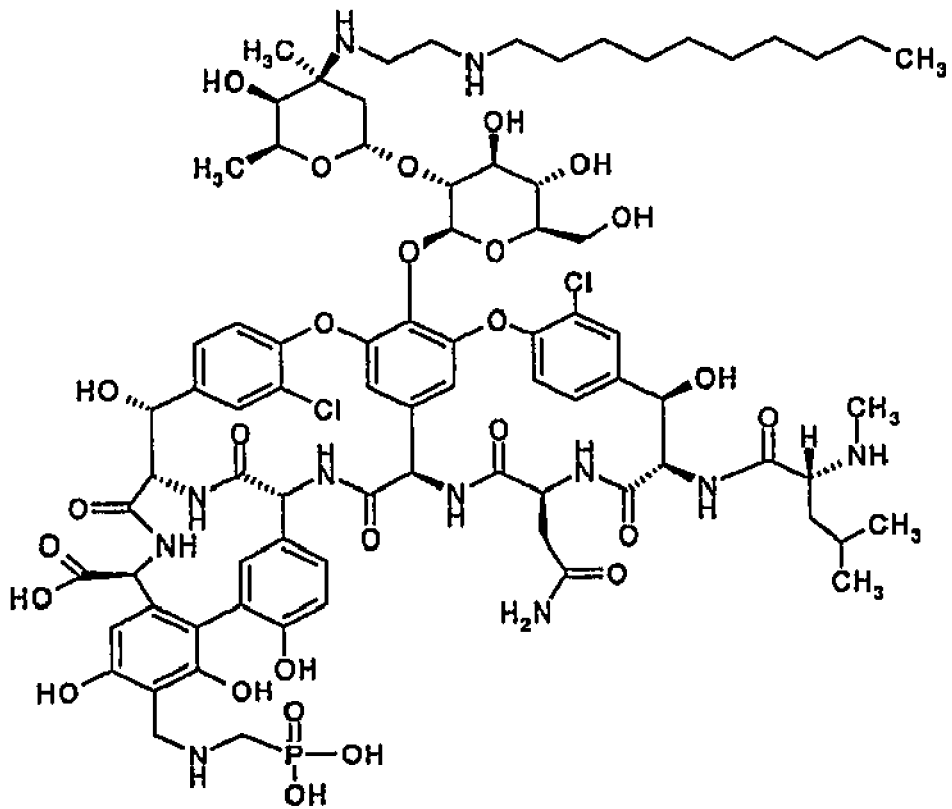

UNITED STATES PATENT AND TRADEMARK OFFICE
CERTIFICATE OF CORRECTION

PATENT NO. : 7,208,471 B2
APPLICATION NO. : 11/265570
DATED : April 24, 2007
INVENTOR(S) : Michael R. Leadbetter It is certified that error appears in the above-identified patent and that said Letters Patent is hereby corrected as shown below:

Column 49
at lines 5-38, in Claim 3, replace the structure after "a compound of the formula:" with the following structure:

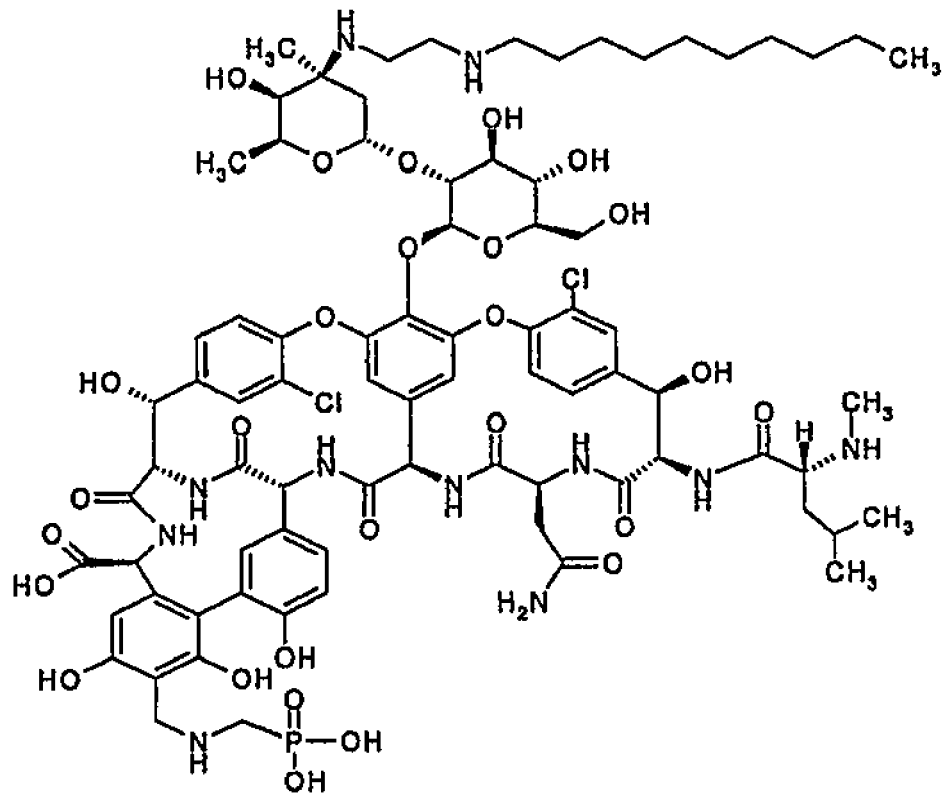

UNITED STATES PATENT AND TRADEMARK OFFICE
CERTIFICATE OF CORRECTION

PATENT NO. : 7,208,471 B2
APPLICATION NO. : 11/265570
DATED : April 24, 2007
INVENTOR(S) : Michael R. Leadbetter It is certified that error appears in the above-identified patent and that said Letters Patent is hereby corrected as shown below:

<u>Columns 49 and 51</u>
at lines 46-65 and lines 1-19, in Claim 4, replace the structure after "a compound of the formula:" with the following structure:

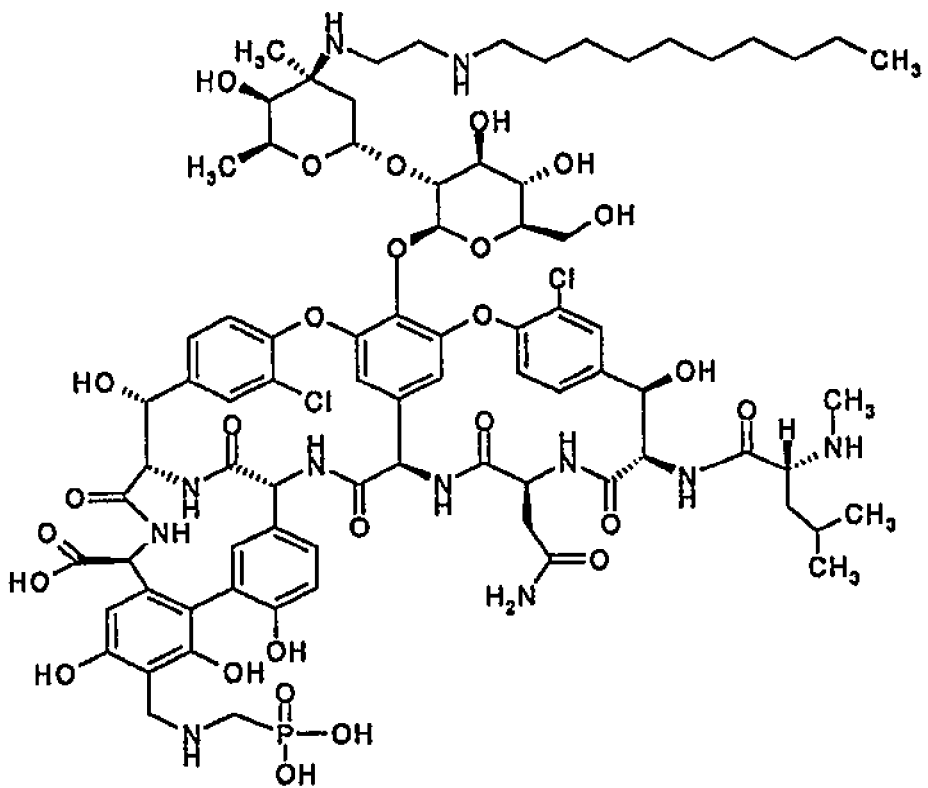

UNITED STATES PATENT AND TRADEMARK OFFICE
CERTIFICATE OF CORRECTION

PATENT NO. : 7,208,471 B2
APPLICATION NO. : 11/265570
DATED : April 24, 2007
INVENTOR(S) : Michael R. Leadbetter It is certified that error appears in the above-identified patent and that said Letters Patent is hereby corrected as shown below:

<u>Columns 51</u>
at lines 25-58, in Claim 5, replace the structure after "a compound of the formula:" with the following structure:

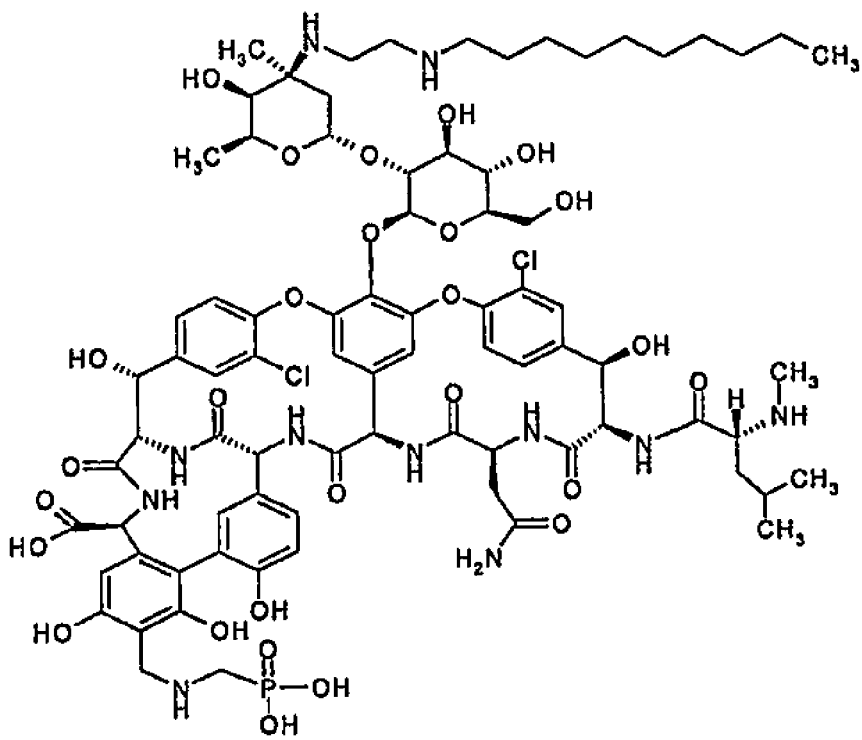

Signed and Sealed this

Twenty-first Day of August, 2007

JON W. DUDAS
*Director of the United States Patent and Trademark Office*